United States Patent
Uemura et al.

(10) Patent No.: US 6,627,155 B1
(45) Date of Patent: Sep. 30, 2003

(54) COMBUSTION FURNACE SYSTEM FOR ANALYZING ELEMENTS IN A SAMPLE

(75) Inventors: Takeshi Uemura, Miyanohigashi-machi (JP); Akihiro Hirano, Miyanohigashi-machi (JP); Juichiro Ukon, Miyanohigashi-machi (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/328,684

(22) Filed: Jun. 9, 1999

(30) Foreign Application Priority Data

Jun. 12, 1998  (JP) .......................... 10-181647
Jul. 10, 1998  (JP) .......................... 10-196241
Jul. 10, 1998  (JP) .......................... 10-196254

(51) Int. Cl.$^7$ ............................................ G01N 31/12
(52) U.S. Cl. .................... 422/83; 422/68.1; 422/80; 422/82.05; 422/82.08; 422/99; 436/155; 436/160; 436/164; 73/19.07; 250/288
(58) Field of Search ............. 422/68.1, 80, 82.05, 422/82.08, 83, 99, 100; 436/106, 119, 155, 160, 164, 173; 73/19.07; 250/288

(56) References Cited

U.S. PATENT DOCUMENTS

| | | | |
|---|---|---|---|
| 3,305,318 A | * | 2/1967 | Bennet |
| 3,904,366 A | * | 9/1975 | Grasenick |
| 3,949,590 A | * | 4/1976 | Boillot ......................... 73/19 |
| 3,985,505 A | * | 10/1976 | Bredeweg |
| 4,192,175 A | * | 3/1980 | Godai et al. .................... 73/19 |
| 4,282,183 A | * | 8/1981 | Bredeweg et al. ............. 422/78 |
| 4,305,906 A | * | 12/1981 | Mikasa et al. ................. 422/62 |
| 4,332,591 A | * | 6/1982 | Oi et al. ......................... 422/78 |
| 4,332,770 A | * | 6/1982 | Ishida et al. ................... 422/78 |
| 4,539,645 A | | 9/1985 | Krottinger et al. |
| 4,582,686 A | | 4/1986 | Tsuji |
| 4,877,743 A | * | 10/1989 | Waugh et al. ................ 436/116 |
| 4,916,077 A | * | 4/1990 | Forster et al. ................. 261/76 |
| 5,281,397 A | * | 1/1994 | Ligon et al. ................... 422/89 |
| 5,522,915 A | * | 6/1996 | Ono et al. ..................... 75/385 |
| 5,612,225 A | * | 3/1997 | Baccanti et al. .............. 422/78 |

FOREIGN PATENT DOCUMENTS

| | | |
|---|---|---|
| FR | 2178555 | 11/1973 |
| FR | 2186142 | 1/1974 |
| FR | 2734363 | 11/1996 |
| GB | 1591368 | 6/1981 |
| GB | 2314155 | 12/1997 |

OTHER PUBLICATIONS

"Determination of Carbon in Silicon and Germanium by Combustion in Oxygen While Suspended in an Electromagnetic Field," by N. Larin et al., Journal of Analytical Chemistry of the USSR, vol. 22, No. 4, 1977.

"Reductive Pyrolysis for the Determination of Aqueous Sulfur Compounds with a Helium Microwave–Induced Plasma," by J. Alvarado et al., Analytical Chemistry vol. 65, No. 22, Nov. 15, 1993.

"One–Line Sulfur–Isotope Determination Using an Elemental Analyzer Coupled to a Mass Spectrometer," by A. Gieseman et al., Analytical Chemistry, vol. 66, No. 18, Sep. 15, 1994.

* cited by examiner

*Primary Examiner*—Jill Warden
*Assistant Examiner*—Kathryn Bex

(57) ABSTRACT

The present invention discloses a system for analyzing elements contained in a sample in very slight amounts, such as C, S, O, N, H and the like in materials, such as steel and ceramics. An element analyzer can gasify the sample elements in an appropriate gas, such as oxygen gas in a high-frequency heating furnace or an electric resistant furnace. Resulting gas can be introduced into a mass spectrometer to permit a quantitative analysis of the sample elements. A metal sample can be levitated and heated and melted with induction current for producing the resultant gas for introduction to a mass spectrometer.

10 Claims, 19 Drawing Sheets

COMBUSTION FURNACE SYSTEM FOR ANALYZING ELEMENTS IN A SAMPLE

BACKGROUND OF THE INVENTION

1. Field of the Invention

The present invention relates to a system for analyzing elements of C (carbon), S (sulfur), O (oxygen), N (nitrogen), H (hydrogen) and the like contained in slight amounts, respectively, in a material such as steel, and ceramics and more particularly, to a combustion furnace system that can burn a sample and analyze the gaseous ingredients in an improved manner.

2. Description of Related Art

A method obtained by combining a combustion of a sample in an oxygen gas stream with an infrared absorption scan has been generally used for analyzing quantitatively C, and S contained in steel in slight amounts, respectively. While a method obtained by combining a fusion extracting of a sample in an inert gas with an infrared absorption scan or a thermal conductivity test has also been commonly employed as a method for analyzing quantitatively O, N, and H contained in steel in slight amounts, respectively.

More specifically, the combustion method has a steel sample burned while feeding oxygen gas into a heating furnace and the resultant combustion gas, containing $CO/CO_2$ and $SO_2$ produced at that time, is analyzed by a nondispersive infrared analyzer (NDIR). The fusion extraction method has a graphite crucible containing a sample such as steel disposed in a heating furnace, the sample is heated and fused while feeding an inert gas to the combustion chamber, and the $CO_2$ produced at that time is analyzed by a NDIR, while $N_2$ and $H_2$ are analyzed by a thermal conductivity method.

In both of the method s described above, a lower limit of detection for an element in the sample is about 1 wt ppm (although 0.1 wt ppm is possible with respect to H). However, there is a demand for new materials such as metals and ceramics having a higher purity to be employed in recent years, so that the elements, as described above as impurities must exhibit a lower concentration level.

Under these circumstances, the sensitivity of the testing procedures have become insufficient in conventional analyzers as described above, and as a result, a precise determination cannot be effected. In addition, there is also a problem of a false or blank value due to possible contamination of a graphite crucible, so that an accurate determination in the region of very slight amounts of impurities becomes difficult.

Although there is known an ICP-MS method and the like as one type of analyzing method for analyzing steel and the like by the use of a mass spectrometer, it is difficult to realize a measurement with sufficiently high sensitivity, because a large amount of a major component (for example, Fe) of the sample material enters the mass spectrometer, so that the potential excellent resolving power and excellent sensitivity in the order of a ppb which could be derived from a mass spectrometer cannot be easily achieved.

Other examples of combustion furnaces for burning a sample to be analyzed can be found in U.S. Pat. No. 5,110,554, U.S. Pat. No. 3,936,587, U.S. Pat. No. 4,087,249. U.S. Pat. No. 4,234,541 and U.S. Pat. No. 5,236,353.

There is still a desire in the prior art to optimize the ability to measure very minute amounts of elements in a sample in an economical and efficient manner.

SUMMARY OF THE INVENTION

An object of the present invention is to provide a system for analyzing elements contained in a sample (hereinafter referred to simply and optionally as an "element analyzer") by which elements of C, S, O, N, H and the like which may be contained in very slight amounts, respectively, in a sample material such as steel, ceramics and the like can be quantitatively analyzed with high sensitivity.

In order to attain the above described object, the element analyzer according to a first embodiment is constituted so that a sample is burned up while feeding oxygen gas into a high-frequency heating furnace or an electric resistance furnace, and the gas produced at that occasion is introduced to a mass spectrometer, thereby to analyze quantitatively at least any one element of C, S, and N.

An element analyzer according to a second embodiment uses a graphite crucible containing a sample. The crucible is placed into an impulse furnace, and the sample is heated and fused while feeding an inert gas into the furnace. The resultant gas is extracted and introduced into a mass spectrometer, thereby to analyze quantitatively at least one element, such as O, N, and H that may be contained in the sample.

Furthermore, an element analyzer according to a third embodiment has the sample heated while feeding a hydrogen gas to an electric resistance furnace, and the gas produced at that occasion is introduced into a mass spectrometer, thereby to analyze quantitatively at least any one of C, S, and N.

In any of the above described element analyzers, the desired elements to be measured can be analyzed quantitatively with high sensitivity. The mass spectrometer can concentrate its excellent resolving power at specific components to be measured thereby to achieve a measurement with higher sensitivity, over that of the prior art, as a result of removal of oxidized dust by means of a dust filter, removal of water vapor (moisture) by means of a dehumidifier, and oxidation of CO into $CO_2$ by means of an oxidizing device.

In any of the above described element analyzers, it may be alternately arranged so that a gas initially produced in a furnace is again supplied to the furnace through a re-circulating passageway before the final combustion or extraction of the sample, and the above described gas is then supplied to the mass spectrometer after completing the combustion or extraction. According to such an arrangement, stable measured results can be obtained in a single procedure of testing.

An element analyzer according to a fourth embodiment is constituted in such a manner that a laser beam of an appropriate intensity is irradiated upon a metal sample, which is disposed in an irradiation cell, to which is selectively introduced oxygen gas or an inert gas, and a gas produced at that occasion is then introduced to a mass spectrometer to analyze quantitatively at least any one of carbon, sulfur, nitrogen, and hydrogen contained in the metal sample.

Moreover, an element analyzer according to a fifth embodiment has a laser beam irradiating a metal sample which has been disposed in an irradiation cell to which is introduced oxygen gas, and a gas produced at that occasion is introduced to a mass spectrometer, thereby to analyze quantitatively either of carbon, and sulfur contained in the metal sample.

Still further, an element analyzer according to a sixth embodiment is constituted so that a laser beam is irradiated upon a metal sample disposed in an irradiation cell to which is introduced an inert gas, and a gas produced at that occasion is introduced to a mass spectrometer, thereby to analyze quantitatively either of nitrogen and hydrogen contained in the metal sample.

Yet further, an element analyzer according to a seventh embodiment is constituted so that a laser beam is irradiated upon a metal sample disposed in an irradiation cell to which are introduced hydrogen gas and an inert gas at a predetermined ratio, and a resultant gas produced at that occasion is introduced to a mass spectrometer, thereby to analyze quantitatively at least any one of carbon, sulfur, and nitrogen contained in the metal sample.

In the above described element analyzers according to the fourth to the seventh embodiments, desired elements can be analyzed quantitatively with high sensitivity. The mass spectrometer can concentrate its excellent resolving power at components to be measured and thereby achieve measurement with higher sensitivity as a result of removal of oxidized dust by means of a dust filter, and removal of water vapor (moisture) by means of a dehumidifier.

An element analyzer according to an eighth embodiment is constituted so that either one of an inert gas and an oxygen gas can be supplied to an extracting cell around which has been wound a high-frequency coil. While the high-frequency coil is energized, the metal sample is maintained in position inside the extracting cell by means of high-frequency levitation, at the same time, the sample is heated and fused, and the gas produced at that occasion is conveyed and carried by the inert gas or the oxygen gas to the mass spectrometer, thereby to analyze quantitatively therein at least one of carbon, sulfur, nitrogen, and hydrogen contained in the metal sample.

Furthermore, the element analyzer according to a ninth embodiment is constituted so that oxygen gas is supplied to an extracting cell around which has been wound a high-frequency coil. When the high-frequency coil is energized, the metal sample is maintained at an elevated position inside the extracting cell by means of high-frequency levitation, at the same time, the sample is heated and fused, and the gas produced at that occasion is conveyed and fed to the mass spectrometer by means of the oxygen gas, thereby to analyze quantitatively therein at least one of carbon, sulfur, and nitrogen contained in the metal sample.

In addition, it may be arranged in the above described eighth and the ninth embodiments that the high-frequency coil is moved vertically along the longitudinal direction of the extracting cell.

In the above described element analyzers according to the eighth and the ninth embodiments, desired elements can be analyzed quantitatively with high sensitivity. The mass spectrometer can concentrate its excellent resolving power at components to be measured to achieve measurement with higher sensitivity as a result of removal of. oxidized dust by means of a dust filter and removal of water vapor (moisture) by means of a dehumidifier.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved combustion furnace system for analyzing elements in a sample.

Figure 1:
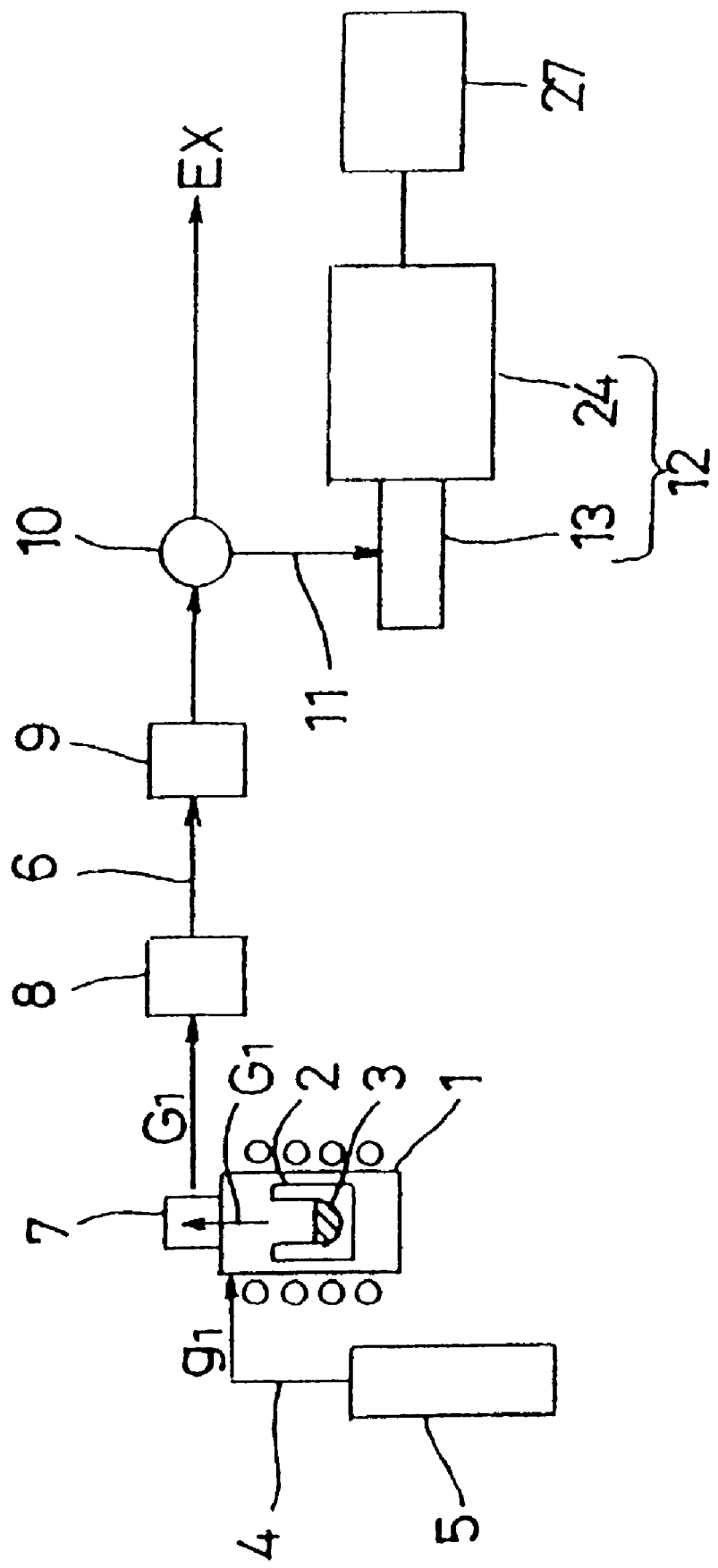
FIG. 1 is a view showing schematically an example of the system for analyzing elements according to a first embodiment.

Preferred embodiments of the invention will be described hereinafter by referring to the accompanying drawings wherein FIGS. 1 through 3 indicate a first embodiment of the invention. FIG. 1 shows schematically an example of a system for analyzing elements wherein the system can analyze quantitatively at least any one element of C, S and N. In FIG. 1, reference numeral 1 designates a high-frequency heating oven as a heating source and 2 is a porcelain crucible to be set in the high-frequency heating oven 1, in the interior of which is contained a sample 3 which has been weighed. Reference numeral 4 is an oxygen gas feed passage for feeding oxygen gas $g_1$ to the high-frequency heating oven 1, and 5 is an oxygen gas cylinder, respectively.

A flow channel 6 provides a passageway through which a gas $G_1$ produced as a result of burning up the sample 3 in the high-frequency heating oven 1, flows. The gas flow channel 6 is provided with a dust filter 7 for removing any oxidized dust such as iron oxide contained in the produced gas $G_1$, a dehumidifier 8 for removing water vapor (moisture) contained in the produced gas $G_1$, and an oxidizing device 9 for oxidizing CO contained in the produced gas $G_1$, into $CO_2$, a sampling section 10 is disposed on the downstream side of these stations. Furthermore, the sampling section 10 is coupled to an exhaust section (not shown), and joined to a mass spectrometer (for example, Q-MS) 12 through a flow channel 11.

Figure 2:
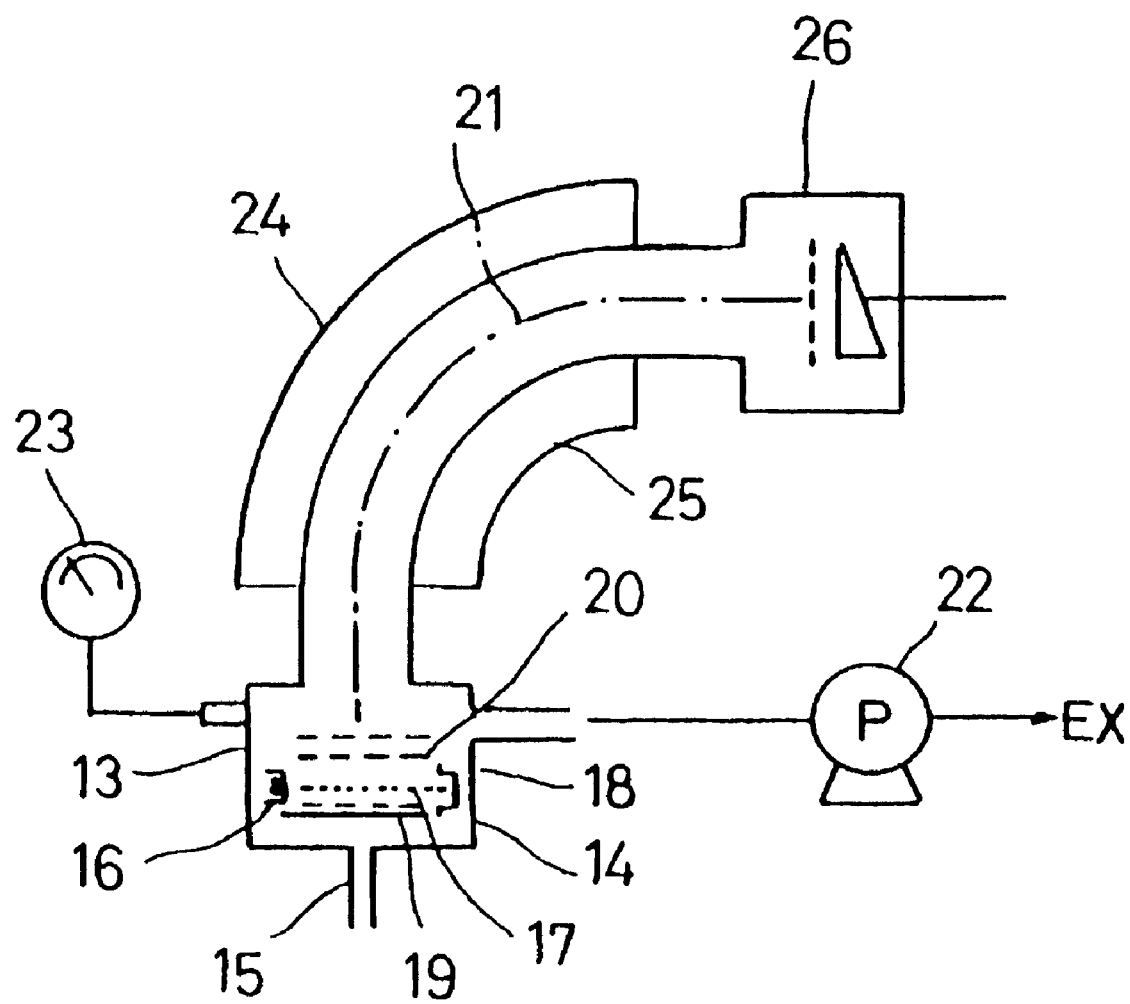
FIG. 2 is a view showing an example of the mechanical features of a spectrometer used in the above described system for analyzing elements.

FIG. 2 is a view showing an example of the mass spectrometer 12 wherein an ionizing section 13 having a filament 16 is disposed on one side of a gas inlet 15 which is connected to the flow channel 11 in such a manner that the filament is opposed to an electron collecting electrode 18 for collecting electrons 17 produced at the time when the filament 16 is heated in a container 14 maintained at a high vacuum. An ion producing electrode 19, and an ion extracting electrode 20 are further disposed. in the container 14, thereby producing ions 21. Reference numeral 22 denotes an exhaust pump for drawing a gas contained inside the container 14 at a high degree of vacuum, arid 23 denotes a pressure gage, respectively. An analyzing section 24 extends from the above described ionizing section 13, and is encompassed with a magnet member 25 for generating a magnetic field. An ion collector 26 collects the ions 21 which have passed through the analyzing section 24.

While the ionic current obtained by the ion collector 26 has not been illustrated in the drawing, it is input to a control unit (for example, computer) 27 through a pre-amplifier, a main amplifier, and an A/D converter, and the ionic current thus input is suitably processed therein.

Operation of a system for analyzing elements having the above constitution can be described by referring also to FIG. 1, wherein steel is used as a sample 3. The sample 3 is weighed and contained in the porcelain crucible 2, and the porcelain crucible 2 containing the sample 3 is set in the high-frequency heating oven 1. The sample 3 is heated and burned while supplying oxygen gas g, to the high-frequency heating oven 1. The gas $G_1$ produced as a result of the burning contains CO, $CO_2$, $SO_2$, $NO_2$, and water vapor.

The produced gas $G_1$ is introduced into the flow channel 6 by means of the oxygen gas $g_1$, as a carrier gas, and the produced gas flows towards the downstream side thereof. In mid course thereof, the produced gas is subjected to pre-treatments such as removal of oxidized dust, such as iron oxide, by a dust filter 7, removal of water vapor in the dehumidifier 8, and further CO is oxidized into $CO_2$ in an oxidizing device 9. Accordingly, the gas $G_1$, in the former part of the sampling section 10 contains $CO_2$, $SO_2$, and $NO_2$ as components.

The produced gas $G_1$, containing the above described $CO_2$, $SO_2$, and $NO_2$ is sampled at a constant interval and constant amounts in the sampling section 10, and these samples are fed to the ionizing section 13 of the mass spectrometer 12. In the ionizing section 13, $CO_2$, $SO_2$, and $NO_2$ are ionized to $CO_2+(m/z=44)$, $SO_2+(m/z=64)$, and $NO_2+(m/z=48)$, respectively, and they are subjected to a mass spectrometric analysis in the analyzing section 24.

Figure 3:
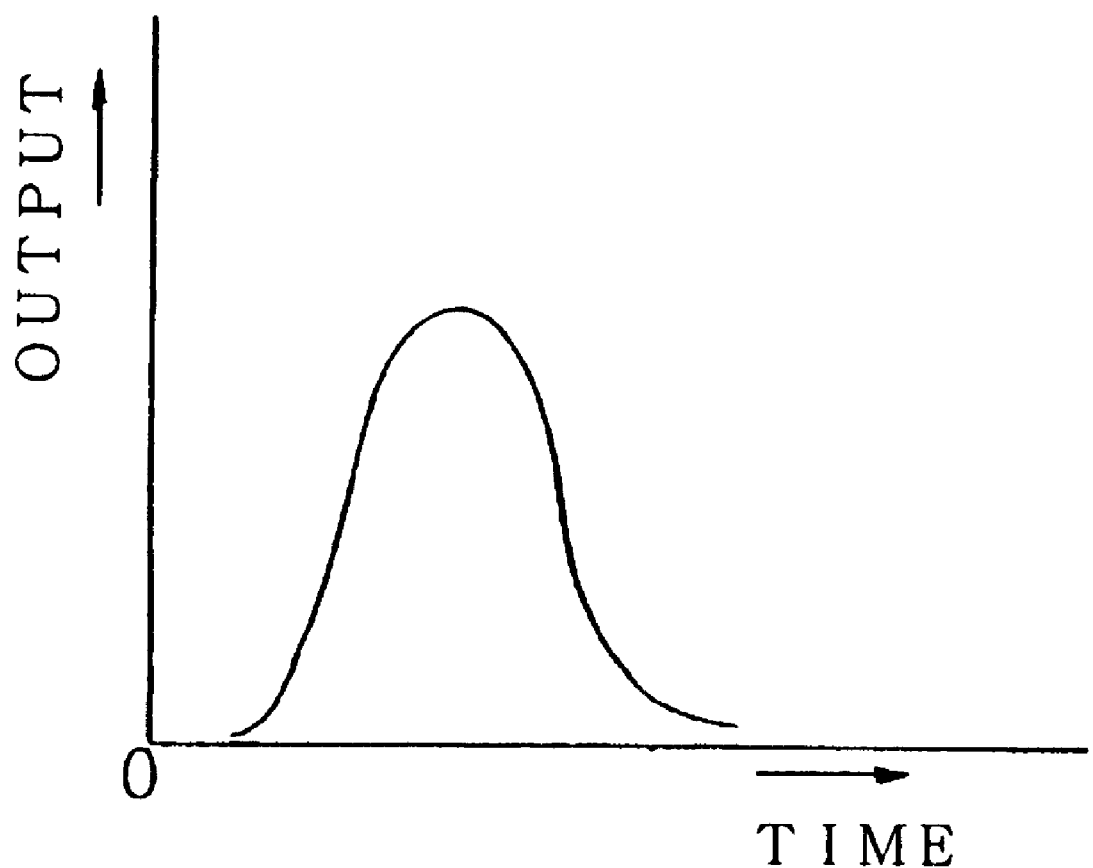
FIG. 3 is a graphical representation schematically showing an example of a mass spectrum of $CO_2+$ obtained in the above described system for analyzing elements.

FIG. 3 is a graphical representation showing schematically a graphic example of a mass spectrum of $CO_2+$ obtained by the system for analyzing elements having the above described constitution wherein the mass spectrum varies with time in response to a burning pattern of the sample 3. Since a value of the mass spectrum integrated, is proportional to an amount of C contained in the sample 3, the C in the sample 3 can be determined on the basis of the value integrated.

Furthermore, since the mass spectra are also obtained for $SO_2+$ and $NO_2+$, as in the case of $CO_2+$, C and N in the sample 3, they can be determined, as a matter of course, by integrating these mass spectra in accordance with a similar manner as that described above.

Since the gas $G_1$, produced in the high-frequency heating oven $_1$ is suitably pretreated, then the produced gas $G_1$ as supplied to the mass spectrometer 12 may contain elements such as C, S, and N which are merely slight amounts thereof (at a degree of ppm or less) yet they can be positively and precisely determined.

Figure 4:
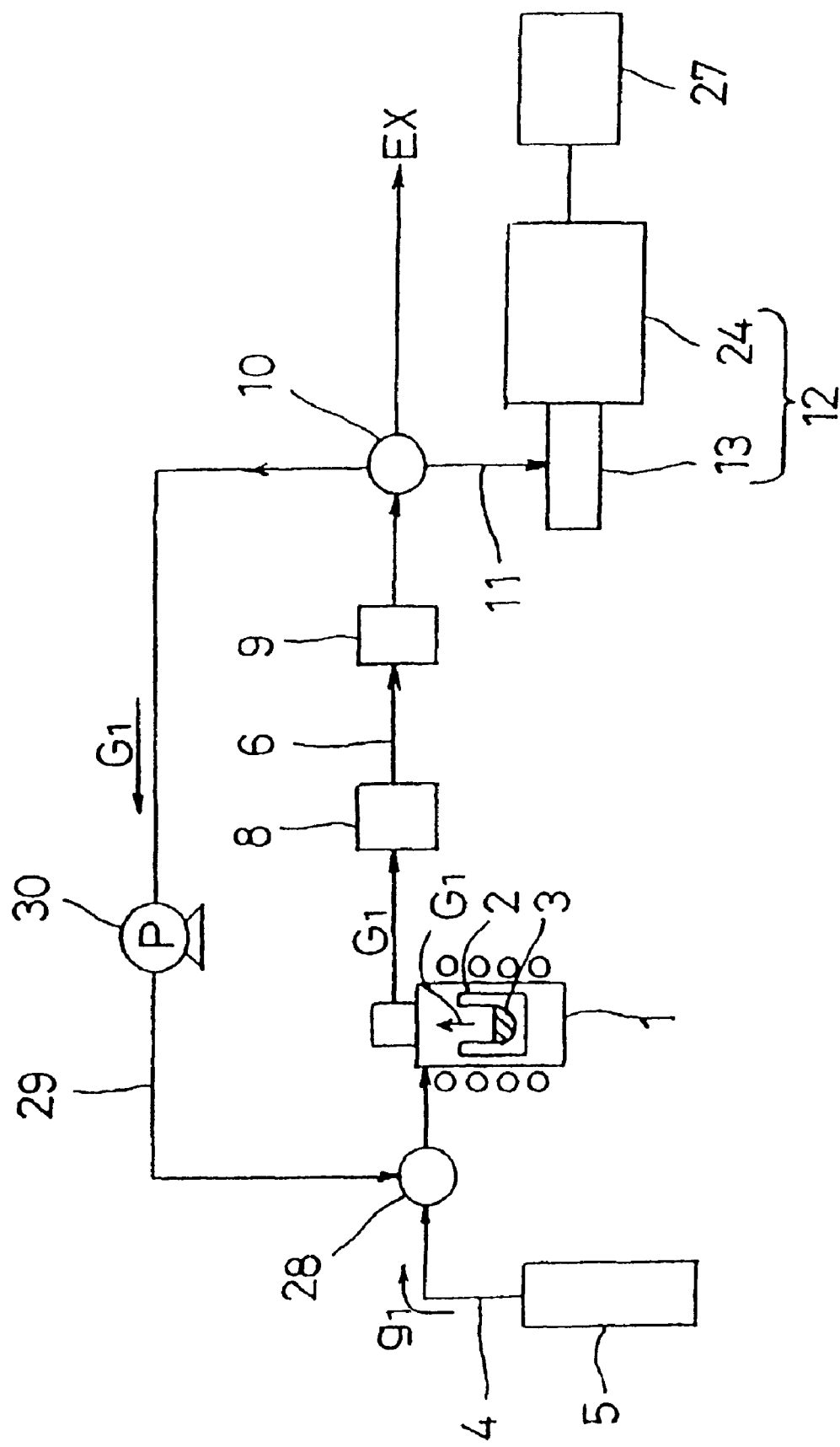
FIG. 4 is a view showing another embodiment of the system for analyzing elements according to the first embodiment.
Figure 5:
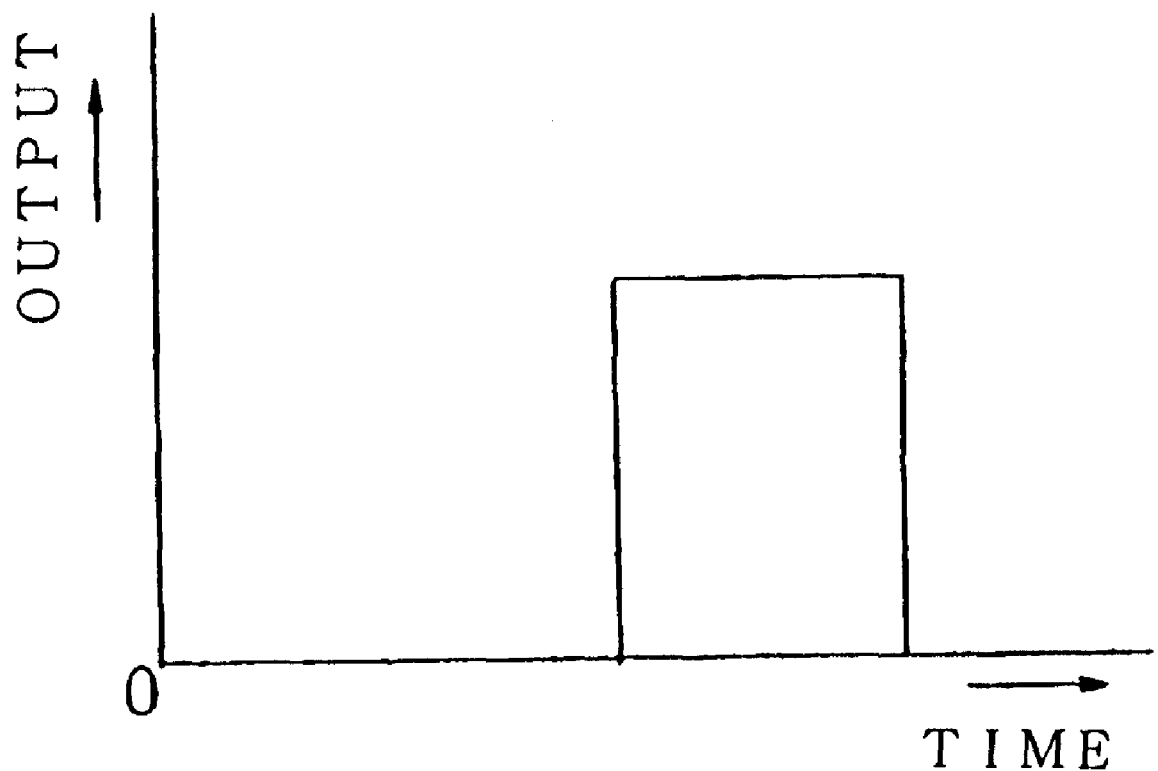
FIG. 5 is a graphical representation showing schematically an example of mass spectrum of $CO_2+$ obtained in the above described system for analyzing elements.

FIGS. 4 and 5 show another preferred embodiment of the above described invention. In a system for analyzing elements according to the present embodiment, a gas $G_1$, produced in a high-frequency heating oven 1 is subjected to a prescribed treatment, and then the gas $G_1$ thus treated is supplied repeatedly to the high-frequency heating oven 1 as shown in FIG. 4. Namely, reference numeral 28 in FIG. 4 designates a switch cock valve disposed in a feed passage 4 for feeding oxygen gas to the high-frequency heating oven 1. Reference numeral 29 denotes a circulating passage for connecting the switch cock valve 28 to a sampling section 10, and is provided with a suction pump 30.

The gas $G_1$ produced in the high-frequency heating oven 1 is fed back to the high-frequency heating oven 1 by an action of the suction pump 30 provided in the circulating passage 29, and the gas $G_1$, output from the high-frequency heating oven 1 is circulated so as to return to the high-frequency heating oven 1 through a flow channel 6, the sampling section 10, the circulating passage 29 and the switch cock valve 28, so that the produced gas $G_1$ further aids in burning up a sample 3 as a supplemental oxygen source. The above-mentioned circulation of the gas $G_1$ is conducted repeatedly until burning of the sample 3 is completed. After the completion of burning, the gas $G_1$, is supplied to the mass spectrometer 12 through the sampling section 10.

Since the gas $G_1$ produced in the high-frequency heating oven 1 is recycled and supplied repeatedly to the high-frequency heating oven 1 through the circulating passage 29 until burning of the sample 3 is completed. In the gas $G_1$, which is fed to the mass spectrometer 12 after completing the burning of the sample 3, a composition in the gas $G_1$, which varies with time is averaged, so that C, S, and N can be determined by conducting a single mass spectrometric analysis. FIG. 5 shows an example of the mass spectrum of $CO_2+$ obtained in the system for analyzing elements arranged as described above.

Figure 6:
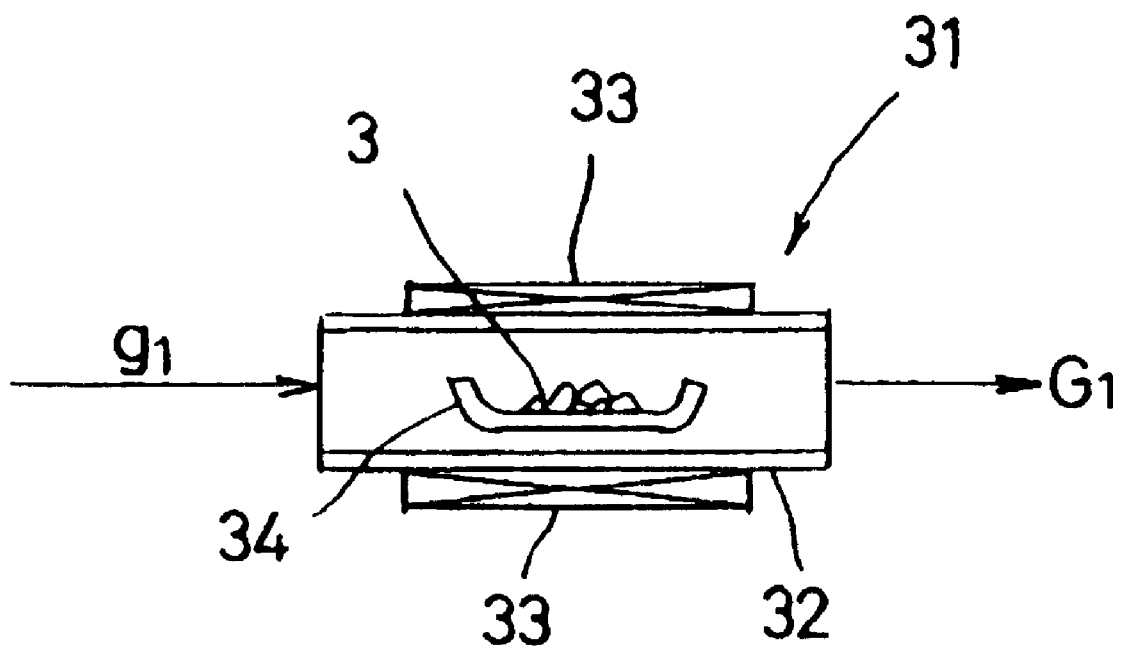
FIG. 6 is a view showing another embodiment of a heating furnace used in the above described system for analyzing elements.

While a heating oven of a high-frequency induction heating type has been used as the heating oven 1 in the above described embodiments, also an electric resistance heating type of oven, as shown in FIG. 6, may be employed. More specifically, a heating furnace 31 shown in FIG. 6 is an electric resistance furnace which is constituted such that a heater 33 is disposed around the outer circumference of a porcelain tube 32, and inside there is placed a porcelain boat 34 (a porcelain crucible may also be used) containing a sample 3.

In place of the above described mass spectrometer 12 of a so-called Q-MS type, a time of flight mass spectrometry (TOF-MS) type may be employed. A TOF-MS type ionizes the target sample and provides a fixed energy to the sample to accelerate it to a detector. The difference in velocity of flight generated from a difference in individual ionic masses enable a detection of the time of flight to obtain a mass spectrum.

In this case, since it is required to sample instantaneously a produced gas $G_1$, it is preferred to arrange a pulse-formed electric field for the produced gas, for example, ionizing the same in the electric field, and only the gas that is ionized is introduced into the TOF-MS.

Figure 7:
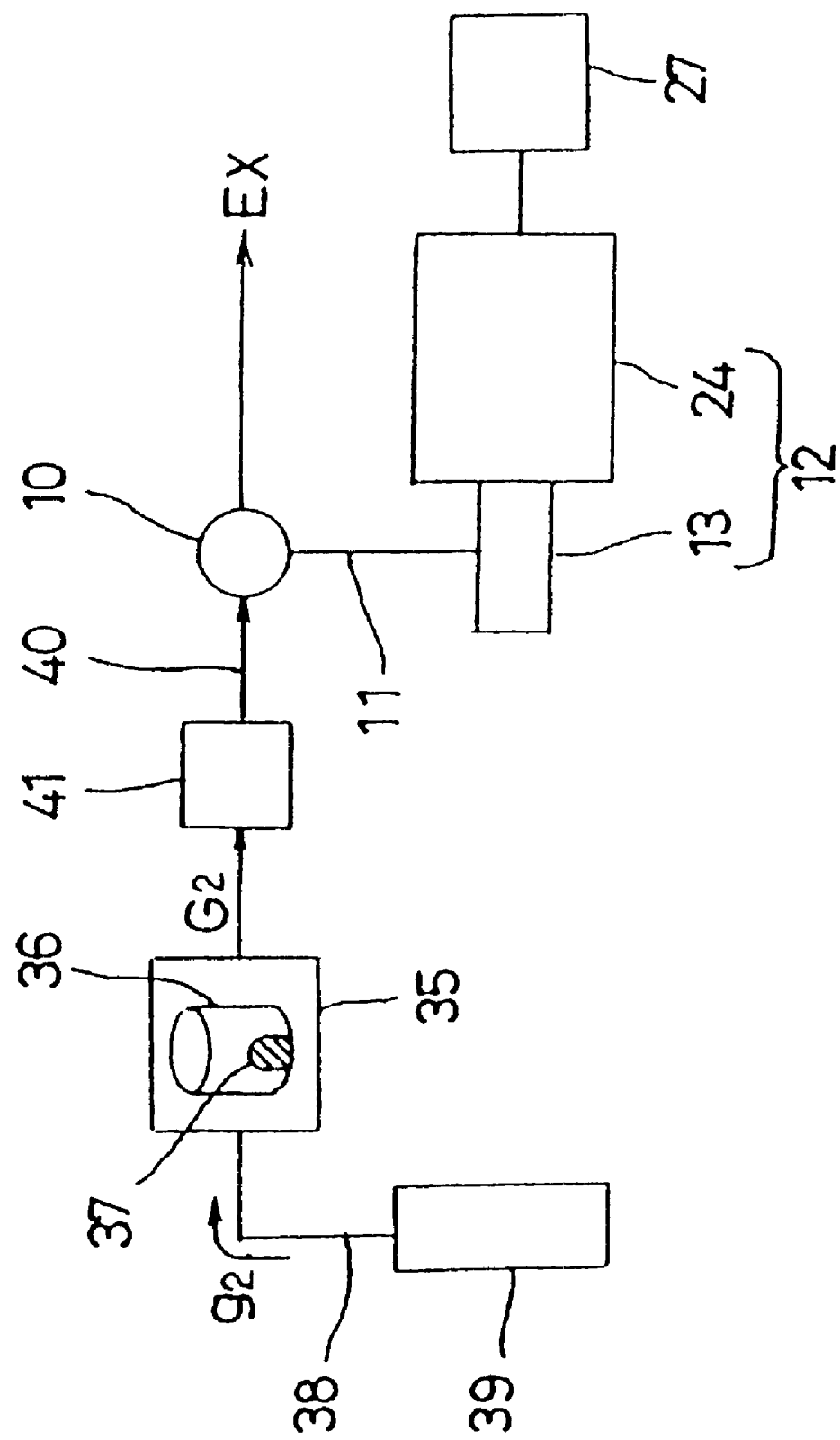
FIG. 7 is a view schematically showing an example of the system for analyzing elements according to a second embodiment.
Figure 8:
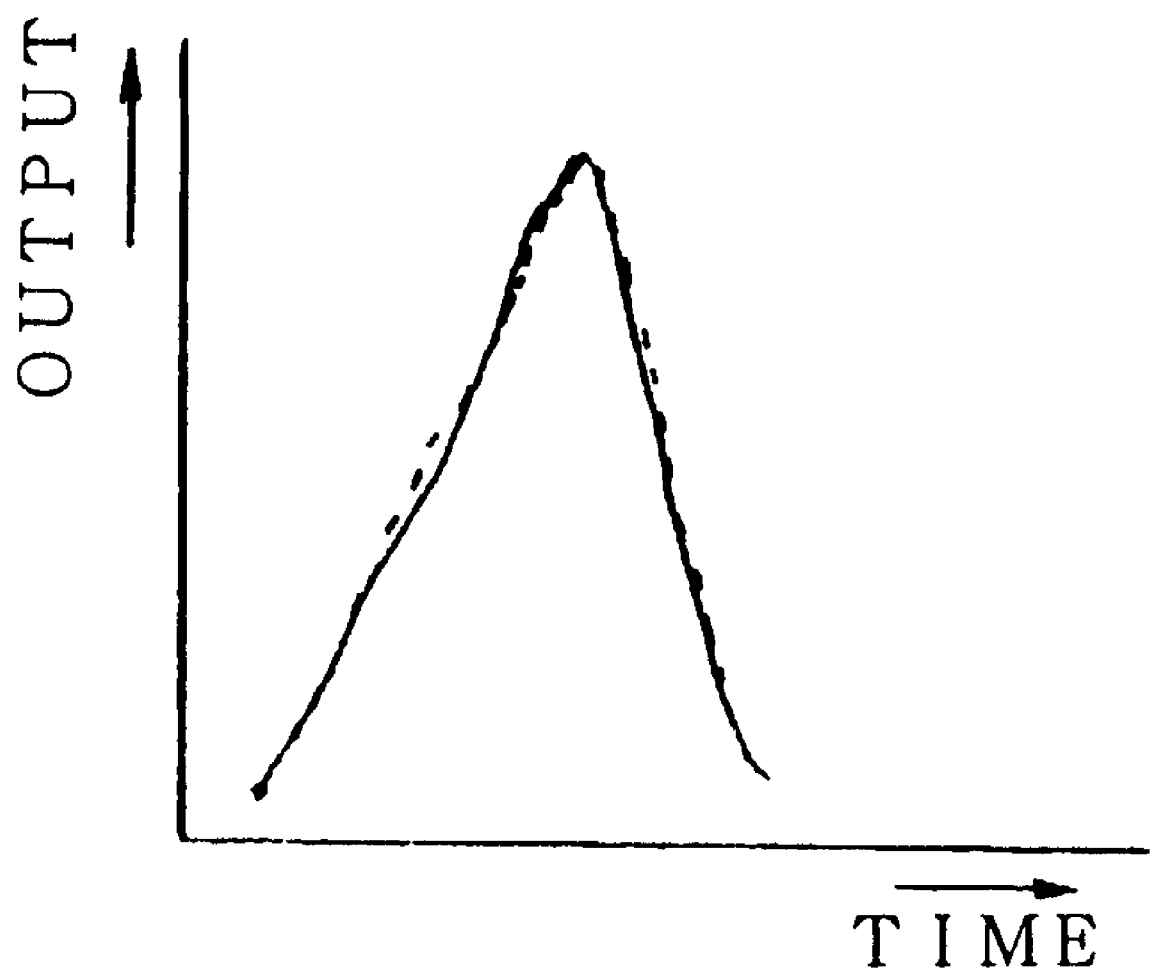
FIG. 8 is a graphical representation showing schematically a mass spectrum of $N+$ obtained in the above described system for analyzing elements.

FIGS. 7 and 8 show a second embodiment of the invention wherein FIG. 7 shows schematically an example of a system for analyzing elements to perform quantitative analysis of at least one of the elements O, N, and H. It is to be noted that a component in FIG. 7 designated by the same reference numeral as that of FIG. 1 is the same component in FIG. 1.

In FIG. 7, reference numeral 35 denotes an impulse furnace as a melting and extracting furnace, 36 a graphite crucible which is to be set in the impulse furnace 35, respectively, and inside which is contained a sample 37 which has been weighed. Reference numeral 38 designates an inert gas feed passage for feeding an inert gas $g_2$ such as argon (Ar) gas, and helium (He) gas to the impulse furnace 35, and 39 an inert gas cylinder, respectively.

Reference numeral 40 designates a flow channel for flowing a gas $G_2$ extracted by heating the sample 37 in the impulse furnace 35, and a dust filter 41 for removing oxidized dust such as iron oxide contained in the gas $G_2$ is disposed downstream in the flow channel, and further downstream thereof is disposed a sampling section 10. One of the portions, on the downstream side of the sampling section 10, is connected to an exhaust section (not shown), while the other portion is connected to a mass spectrometer (for example, Q-MS) 12 through a flow channel 11.

Operation of the element analyzer having the constitution as described above will be described by referring also to FIG. 8 wherein steel is employed as the sample 37. The sample 37 is weighed and placed in the graphite crucible 36, which is then set in the impulse furnace 35. The graphite-crucible 36 is energized while supplying an inert gas (for example, Ar or He) $g_2$ to the impulse furnace 35 to heat the sample 37 at a predetermined temperature. As a result of this heating procedure, O contained in the sample 37 reacts with the graphite crucible 36 to produce CO, while N and H contained in the sample 37 are changed into $N_2$ and $H_2$, respectively. The gas $G_2$ containing these gases CO, $N_2$, and $H_2$ is introduced into the flow channel 40 by means of the inert gas $g_2$ as a carrier gas, and the gas $G_2$ flows towards the side of a downstream thereof. In mid course thereof, the produced gas is subjected to a pretreatment wherein oxidized dust such as iron oxide is removed by the dust filter 41. Accordingly, the gas $G_2$ in the sampling section 10 contains CO, $N_2$, and $H_2$ as its components.

The gas $G_2$ containing the above described CO, $N_2$, and $H_2$ is sampled at a constant interval and a constant amount in the sampling section 10, and these samples are fed to an ionizing section 13 of the mass spectrometer 12. In the ionizing section 13, CO, $N_2$, and $H_2$ are ionized to $CO^+$ (m/z=28), $N^+$ (m/z=14), and $H^+$ (m/z=1), respectively, and they are subjected to mass spectrometric analysis in an analyzing section 24.

FIG. 8 is a graphical representation showing schematically an example of a mass spectrum of N+obtained by the element analyzer having the above described constitution wherein the mass spectrum varies with time in response to an extracting pattern of the sample 37. Since a value of the mass spectrum integrated is proportional to an amount of N contained in the sample 37, N in the sample 37 can be determined on the basis of the value integrated.

Furthermore, since mass spectra are also obtained as to CO+ and H+, as in the case of N+, O and H in the sample 37, they can be determined, as a matter of course, by integrating these mass spectra in accordance with a similar manner as that above. As mentioned above, since the gas $G_2$ extracted in case of heating and melting of the sample 37 in the impulse furnace 35 is suitably pretreated, and then the gas $G_2$ is supplied to the mass spectrometer 12, elements such as O, N, and H which are contained merely in slight amounts thereof (at a degree of ppm or less) can be positively and precisely determined.

Figure 9:
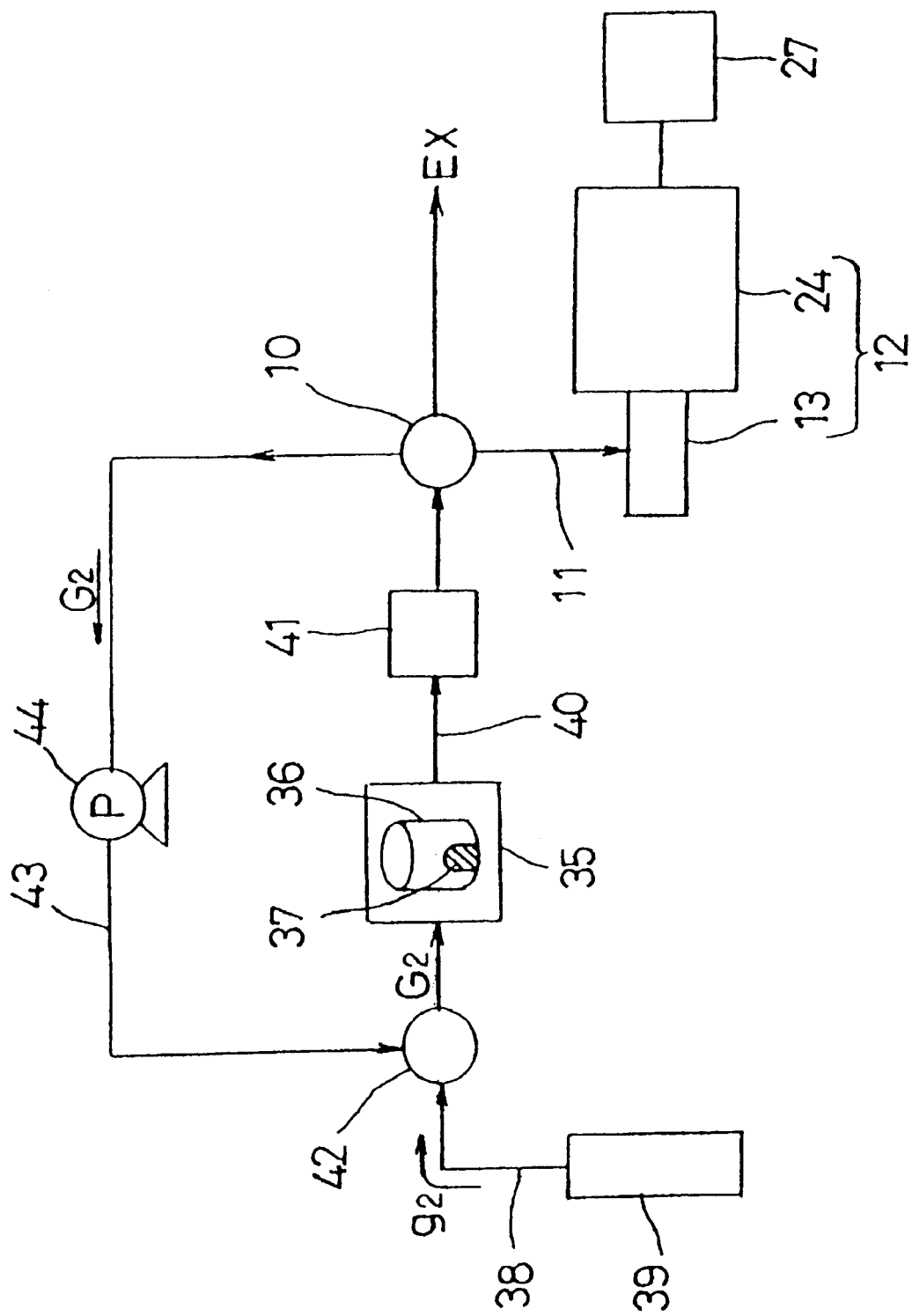
FIG. 9 is a view showing another embodiment of the system for analyzing elements according to the second embodiment.

Furthermore, it may also be arranged, that the gas $G_2$ extracted in the impulse furnace 35 is subjected to a prescribed treatment, and then the so treated gas is supplied repeatedly to the impulse furnace 35. More specifically, FIG. 9 shows another preferred embodiment of the invention wherein reference numeral 42 is a switch cock valve disposed in a feed passage 38 for feeding an inert gas to the impulse furnace 35. Reference numeral 43 denotes a circulating passage for connecting the switch cock valve 42 to a sampling section 10, and is provided with a suction pump 44.

Figure 10:
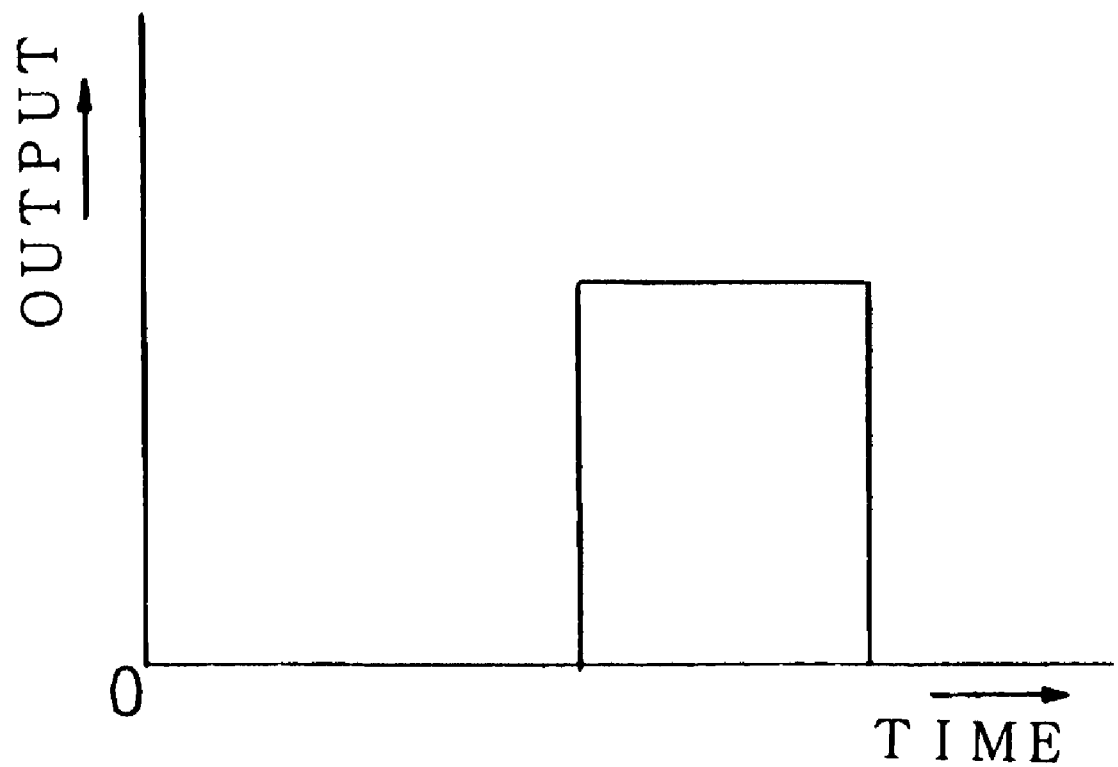
FIG. 10 is a graphical representation showing schematically a mass spectrum of $N+$ obtained in the above described system for analyzing elements.

Since operation of the element analyzer constituted as shown in FIG. 9 is basically the same as that shown in FIG. 7, the details thereof will be omitted. FIG. 10 shows an example of a mass spectrum of $N^+$ obtained in the element analyzer having a constitution as described above.

It is to be noted that a TOF-MS may be employed also as the mass spectrometer 12. In this case, since it is required to sample instantaneously the gas $G_2$, it is preferred to arrange a pulse-formed electric field for ionizing the gas in the electric field, and only the gas ionized is introduced into the TOF-MS.

Figure 11:
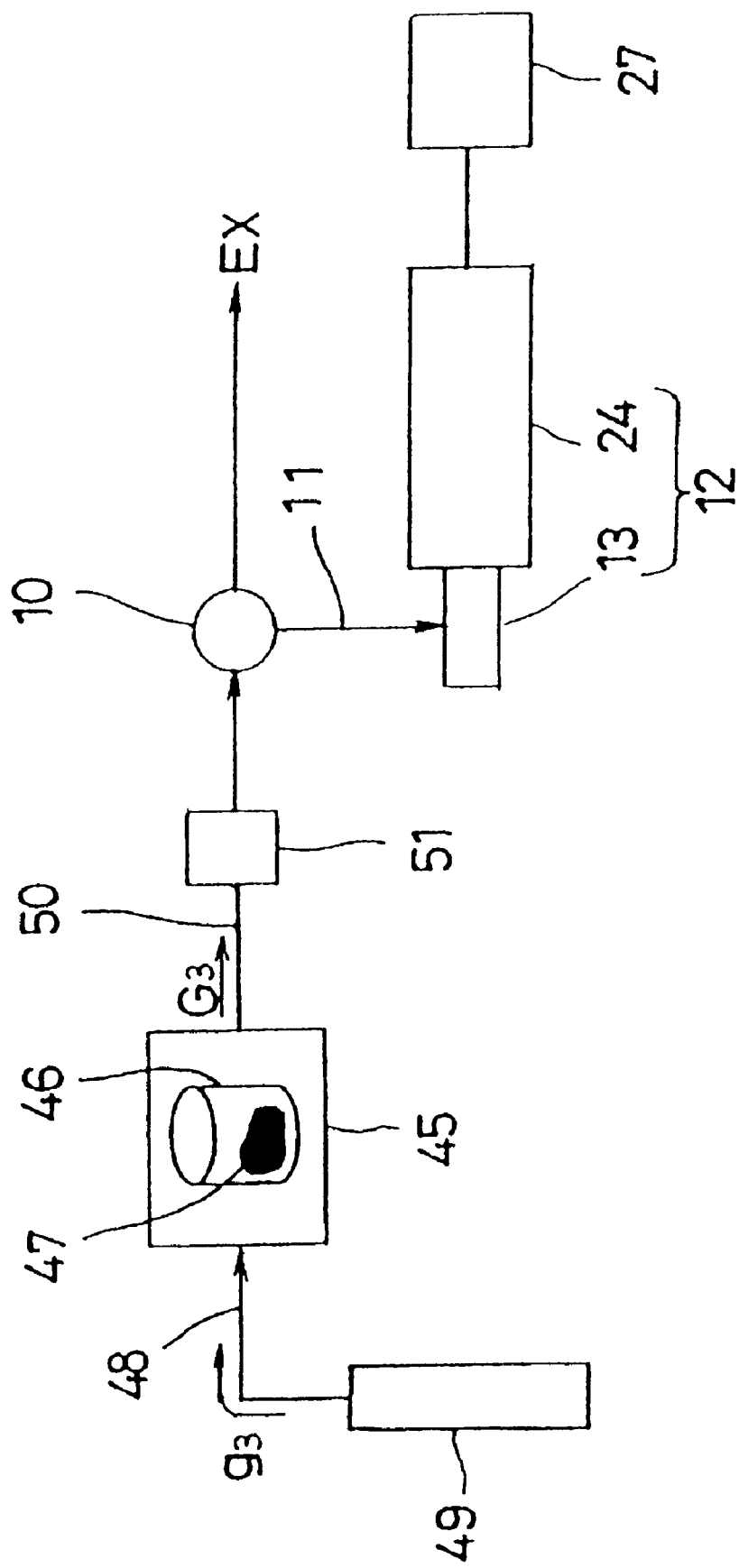
FIG. 11 is a view showing schematically an example of the system for analyzing elements according to a third embodiment.
Figure 12:
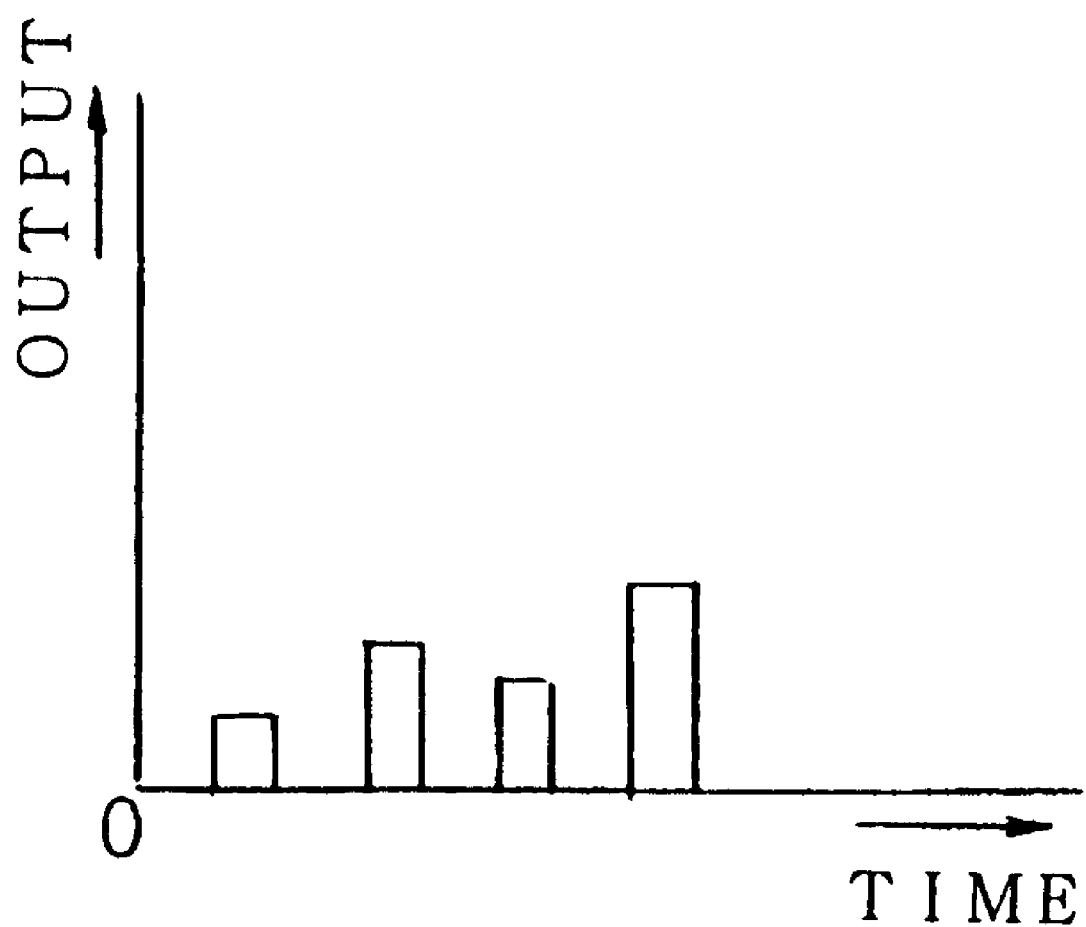
FIG. 12 is a graphical representation showing schematically an example of mass spectrum of $CH4+$ obtained in the above described system for analyzing elements.

FIGS. 11 and 12 show a third embodiment of the invention, respectively, wherein FIG. 11 shows schematically an example of a system for analyzing elements quantitatively of at least any one element of C, S, and N. It is to be noted that a component in FIG. 11 designated by the same reference numeral as that of FIG. 1 is the same component in FIG. 1.

In FIG. 11, reference numeral 45 designates an electric resistance furnace having the same constitution as that of the electric resistance furnace 31, and 46 is a container such as a porcelain crucible which is to be set in the electric resistance furnace 45, respectively, inside of which contains a sample 47 which has been weighed. Reference numeral 48 denotes a hydrogen gas feed passage for feeding hydrogen gas $g_3$ to the electric resistance furnace 45, and 49 is a hydrogen gas cylinder, respectively.

Reference numeral 50 designates a flow channel through which a gas $G_3$ produced by heating the sample 47 in the electric resistance furnace 45, flows to a dust filter 51 for removing foreign matters contained in the produced gas $G_3$. The dust filter 51 is disposed in the flow channel 50, and downstream thereof is disposed a sampling section 10. One of the conduit portions on the downstream side of the sampling section 10 is connected to an exhaust section (not shown), while the other portion is connected to a mass spectrometer (for example, Q-MS) 12 through a flow channel 11.

Operation of the element analyzer having the constitution as described above will be described by referring also to FIG. 12 wherein steel is employed as the sample 47. The sample 47 is weighed and placed in the porcelain crucible 46, which is set in the electric resistance furnace 45. The porcelain crucible 46 is energized while supplying the hydrogen gas $g_3$ to the electric resistance furnace 45 to heat the sample 47 at a predetermined temperature. As a result of this heating procedure, C, S, and N contained in the sample 47 reacts with the hydrogen gas $g_3$ to produce gases of $CH_4$ (methane), $H_2S$ (hydrogen sulfide), and $NH_3$ (ammonia), respectively. The gas $G_3$ containing these gases $CH_4$, $H_2S$, and $NH_3$ is introduced into the flow channel 50 by means of hydrogen gas g3 as a carrier gas, and the gas $G_3$ flows towards the downstream side. In mid course thereof, the gas $G_3$ is subjected to a pretreatment wherein foreign matters such as dust is removed by the dust filter 51. Accordingly, the gas $G_3$ in the former part of the sampling section 10 contains $CH_4$, $H_2S$, and $NH_3$ as its components.

The gas $G_3$ containing the above described $CH_4$, $H_2S$, and $NH_3$ is sampled at a constant interval in constant amounts in the sampling section 10, and these samples are fed to an ionizing section 13 of the mass spectrometer 12. In the ionizing section 13, $CH_4$, $H_2S$, and $NH_3$ are ionized to $CH_4+(m/z=16)$, $H_2S+(m/z=34)$, and $NH_3 +(m/z=17)$, respectively, and they are subjected to mass spectrometric analysis in an analyzing section 24.

FIG. 12 is a graphical representation showing schematically an example of a mass spectrum of $CH_4+$ obtained by the system for analyzing elements having the above described constitution wherein the mass spectrum varies with time in response to a heating and melting pattern of the sample 47. Since a value of the mass spectrum integrated is proportional to an amount of C contained in the sample 47, C in the sample 47 can be determined on the basis of the value integrated.

Furthermore, since mass spectra are also obtained as to $H_2S^+$ and $NH_3^+$, as in the case of the above described $CH_4^+$, S and N in the sample 47 can be determined by integrating these mass spectra in accordance with a similar manner as that described above.

As described above, since the gas $G_3$ produced in the case of heating and melting the sample 47 in the electric resistance furnace 45 is suitably pretreated and then, the gas $G_3$ is supplied to the mass spectrometer 12, elements such as C, H, and N which are contained merely in slight amounts thereof (at a degree of ppm or less) can be positively and precisely determined.

Figure 13:
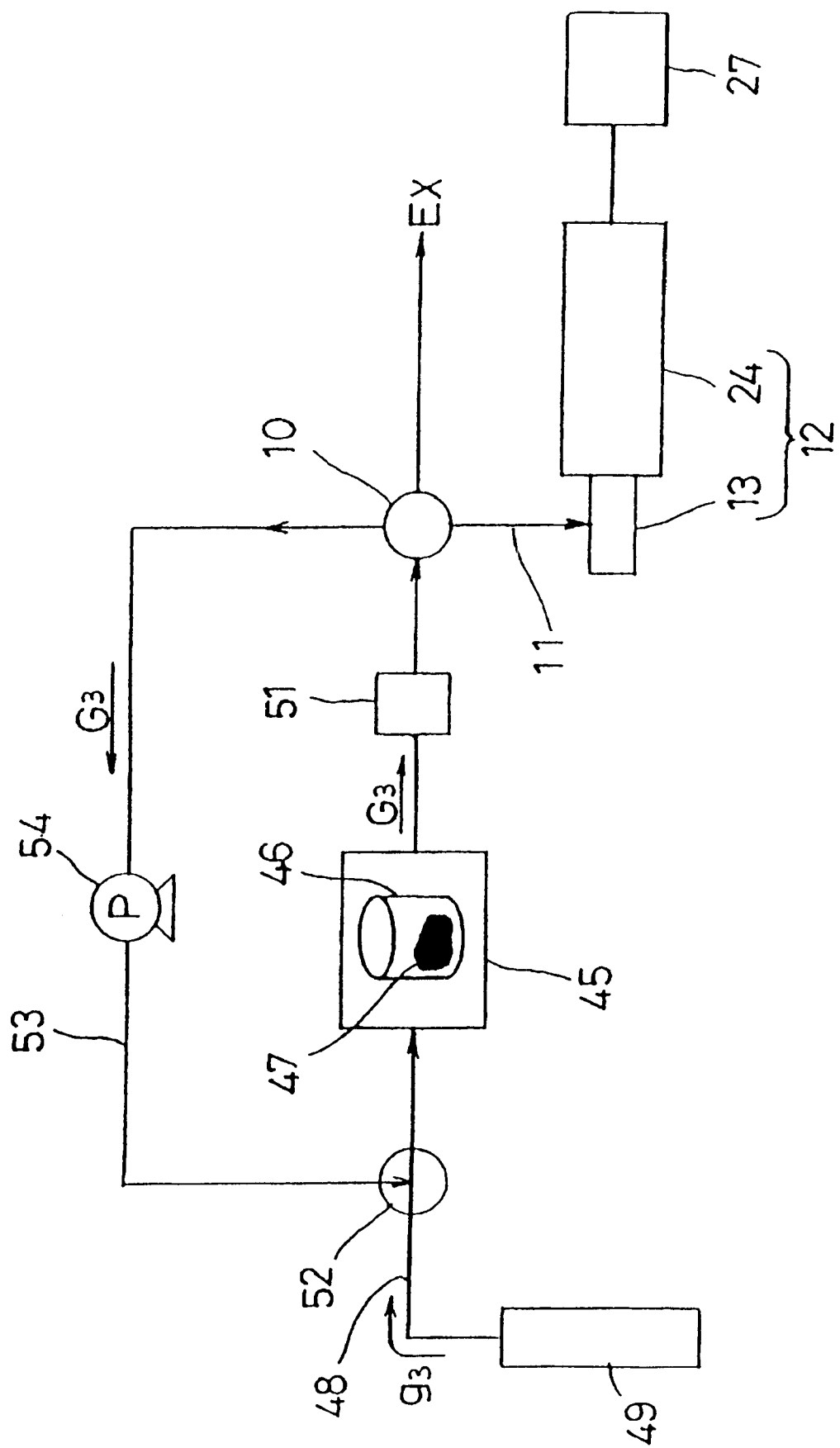
FIG. 13 is a view showing another embodiment of the system for analyzing elements according to the third embodiment.

Furthermore, it may also be arranged that the gas $G_3$ produced in the electric resistance furnace 45 is subjected to a prescribed treatment, and then the treated gas is supplied repeatedly to the electric resistance furnace 45. More specifically, reference numeral 52 in FIG. 13 is a switch cock valve disposed in a feed passage 48 for feeding hydrogen gas to the electric resistance furnace 45. Reference numeral 53 denotes a circulating passage for connecting the switch cock valve 52 to a sampling section 10, and it is provided with a suction pump 54.

Figure 14:
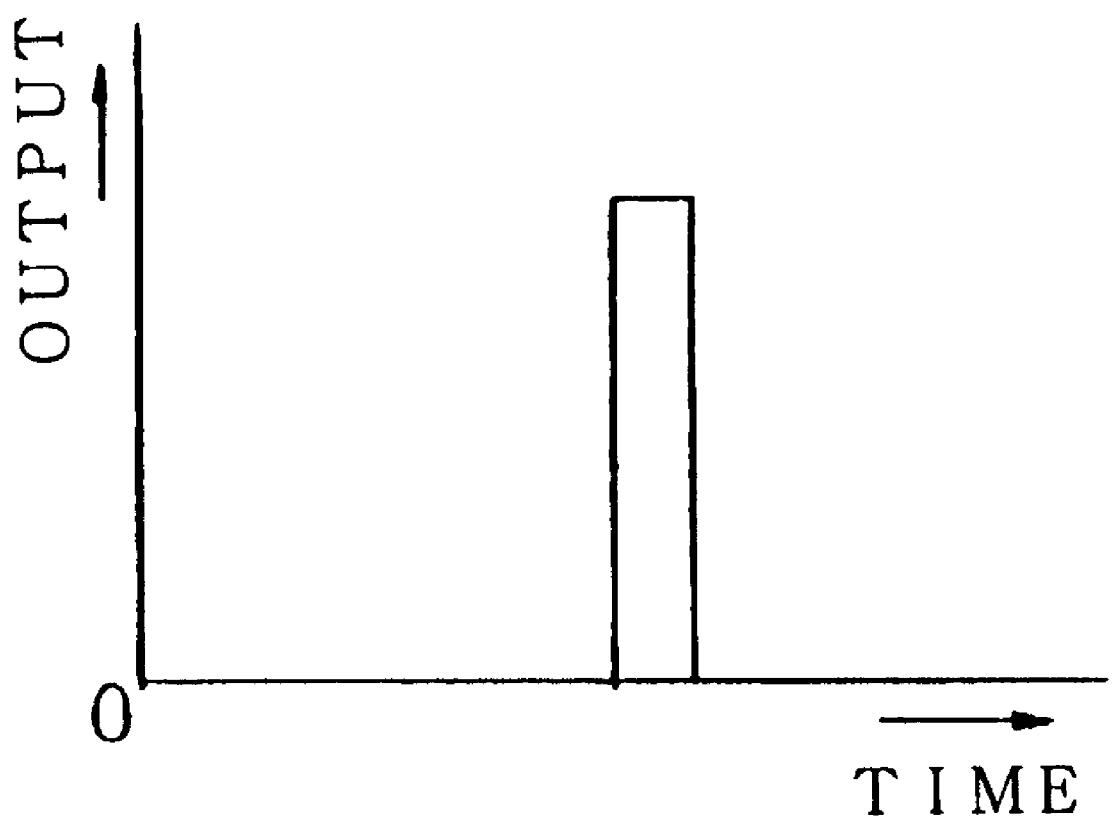
FIG. 14 is a graphical representation showing schematically an example of mass spectrum of $CH_4+$ obtained in the above described system for analyzing elements.

Since operation of the element analyzer constituted as shown in FIG. 13 is the same as that shown in FIGS. 4 and 9, the details thereof will be omitted. FIG. 14 shows an example of a mass spectrum of $CH_4^+$ obtained in the element analyzer having the constitution as described above.

In place of the above described mass spectrometer 12 of a so-called Q-MS type, a mass spectrometer of time of flight (TOF-MS) type may be employed. In this case, since it is required to sample instantaneously the gas $G_3$, it is preferred that a pulse-formed electric field is prepared for ionizing the gas in the electric field, and only the gas ionized is introduced into the TOF-MS. Furthermore, a porcelain boat may be employed in place of the porcelain crucible 46.

Figure 15:
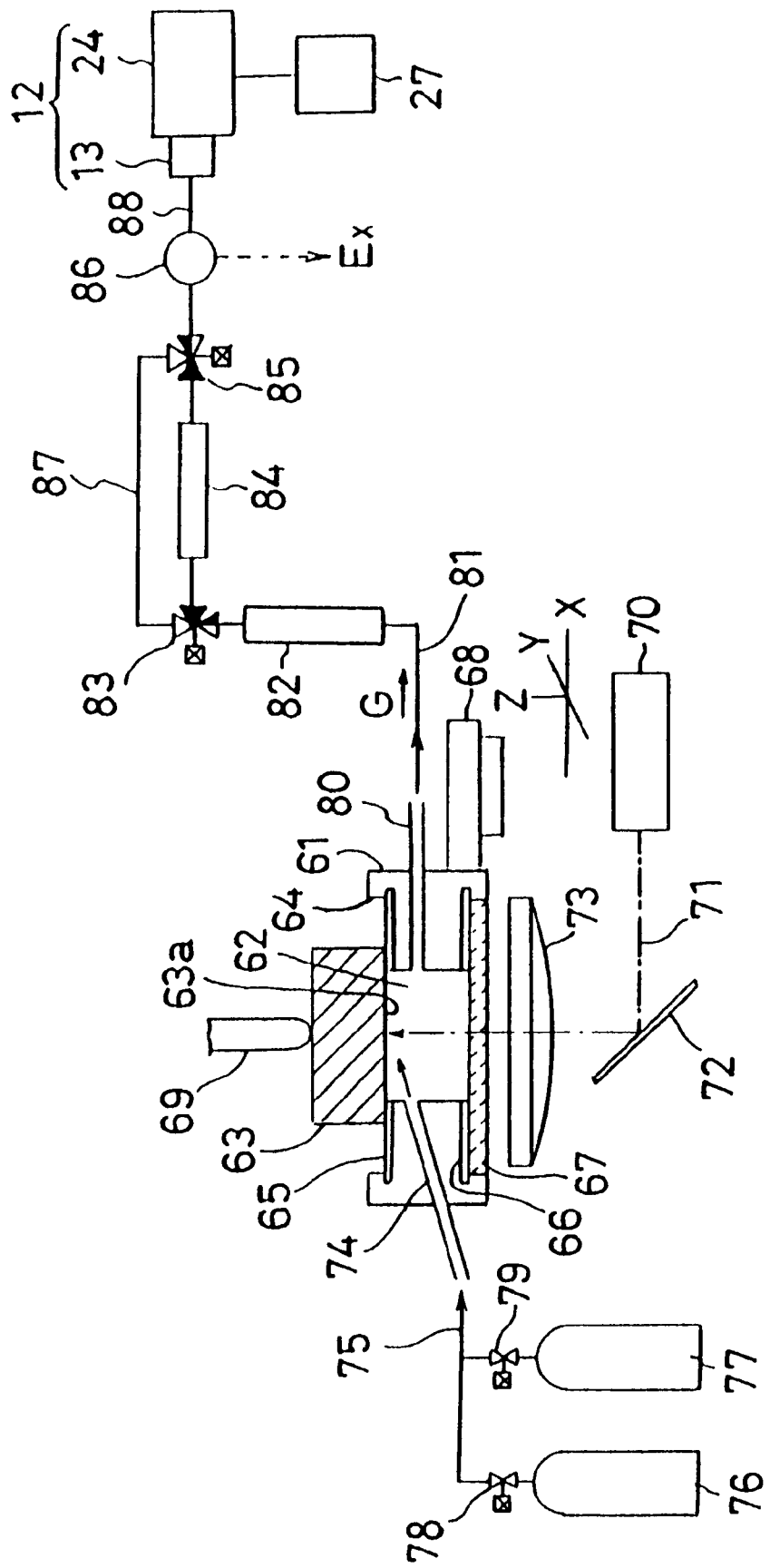
FIG. 15 is a view showing schematically a constitution of the system for analyzing elements in a preferred embodiment according to a fourth embodiment.
Figure 16:
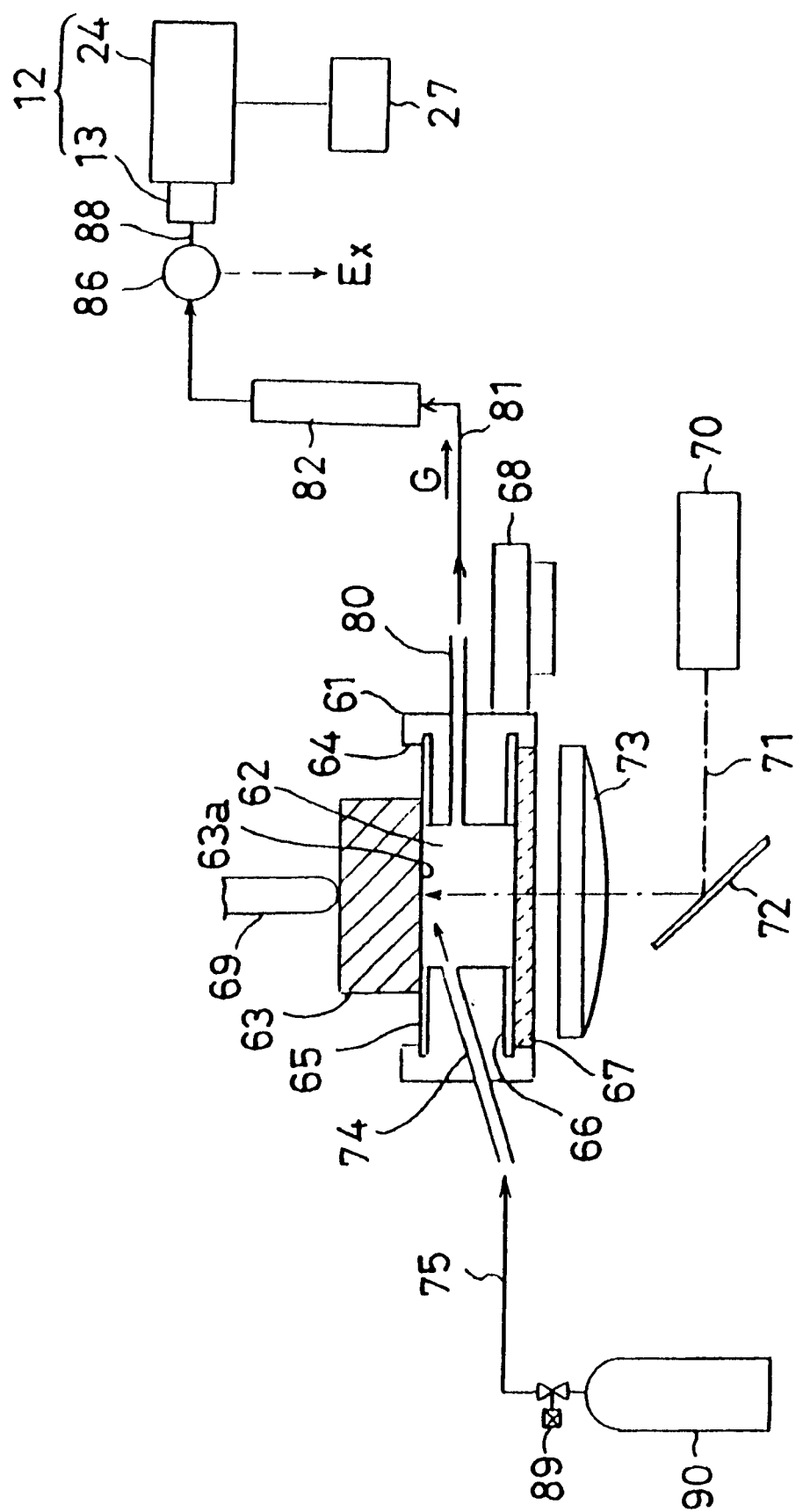
FIG. 16 is a modified example of the above described system for analyzing elements being a preferred embodiment according to the fifth and the sixth embodiments.

FIG. 15 shows another embodiment according to the fourth embodiment, and FIG. 16 shows a preferred embodiment according to a fifth and sixth embodiment, respectively, wherein a system for analyzing elements can analyze quantitatively at least any one element of C, S, N, and H.

In FIG. 15, reference numeral 61 designates a block-shaped irradiation cell the inside of which is defined with a suitable space 62. On the side of the top surface of the irradiation cell 61, a sample resting portion 64 for resting a metal sample 63 such as steel thereon is formed. Reference numeral 65 denotes an annular packing as a sealing member made of, for example, an acid proof synthetic rubber which functions to hold stable the metal sample 63 on the sample resting portion 64. Reference numeral 66 designates an annular packing as a sealing member disposed on the side of the bottom surface of the irradiation cell 61 and which is made from the same material as that of the above described packing 65. Reference numeral 67 denotes a laser beam permeating window which is disposed so as to close the lower opening of the irradiation cell 61. More specifically, when the space 62 in the irradiation cell 61 is closed by the metal sample 63 in the upper part, and by means of the permeating window 67 in the lower part, the space is shut off from the outside. It is to be noted that the irradiation cell 61 can be adjusted by means of a three-dimensional stage 68. More specifically, the three-dimensional stage 68 is constituted so as to be movable along three-dimensional directions, for example, a traverse direction X on the drawing, a vertical direction Y on the drawing, and a Z-direction perpendicular to the direction Y, respectively.

A sample pressing member 69 presses the metal sample 63 and is suitably movable in a vertical direction. A laser oscillator 70 is constituted so that a laser beam 71 output therefrom is irradiated at a predetermined position on the bottom surface 63a of the metal sample 63 through a mirror 72, a condenser lens 73, and the permeating window 67.

A gas jetting nozzle 74 is disposed in an end side of the irradiation cell 61 and functions to jet oxygen gas or an inert gas (such as helium, and argon) to a sample portion which is irradiated by the laser beam 71. The metal sample 63 is placed so as to close the top portion of the cell space 62, and the upstream side of the gas jetting nozzle 74 is joined to an oxygen gas cylinder 76 and an inert gas cylinder 77 through the gas feed passage 75, respectively. Reference numerals 78 and 79 denote valves provided on the gas cylinders 76 and 77, respectively. In other words, it is arranged that either of the oxygen gas and the inert gas may be selectively supplied to the internal space 62 of the irradiation cell 61.

Reference numeral 80 denotes an outlet of a gas G produced in the cell space 2, a gas flow channel 81 communicates with the gas outlet 80. The gas flow channel 81 is provided with a dust filter 82 for removing oxidized dust such as iron oxide contained in the produced gas G, a three-way electromagnetic valve 83, a dehumidifier 84 for removing water vapor (moisture) contained in the produced gas, another three-way electromagnetic valve 85, and a sampling section 86. A gas flow channel 87 connects the three-way electromagnetic valve 83 with the other three-way electromagnetic valve 85 in order to bypass the dehumidifier 84. Either of portions on the downstream side of the sampling section 86 is connected to the above described mass spectrometer 12 through a flow channel 88, while the other portion is connected to an exhaust section (not shown).

In this case, steel is used as a metal sample 63. A steel material to be analyzed is cut out by means of a cutter into a block-shaped piece having a suitable dimension, the cut out surface thereof is ground sufficiently by the use of a sandpaper to prepare the metal sample 63. The metal sample 63 thus prepared is set on the sample resting portion 64 of the irradiation cell 61 in such a manner that a plane 63a thus ground of the metal sample 63 faces the downward direction.

A case where an amount of C or S contained in the steel sample 63 (content) is determined will be described. Before conducting quantitative analysis of elements, purging of air and the like as well as preliminary irradiation of the laser beam are effected. More specifically, the valve 78 is opened to supply oxygen gas to the cell space 62 of the irradiation cell 61, whereby a flow channel extending from the irradiation cell 61 to the mass spectrometer 12 is purged, so that air and the like remaining in the flow channel is exhausted. Thereafter, the laser oscillator 70 is operated to irradiate the laser beam 71 onto the bottom surface 63a of the steel sample 63 under a state where oxygen gas is supplied to the cell space 62, whereby contamination produced at the time of cutting, grinding, or handling of the bottom surface 63a is removed. In the preliminary irradiation for cleaning a sample, it is preferred to irradiate the bottom surface 63a of the steel sample 63 over a wider range than that in case of analysis thereof accordingly the three-dimensional stage 68 is operated to transfer suitably the irradiation cell 61 together with the steel sample 63 in a two-dimensional direction, or to change an angle of the mirror 72.

When the above described preliminary irradiation is completed, the steel sample 63 which has been cleaned is removed from the sample resting portion 64 the steel sample 63 thus removed is weighed, and then it is set on the sample resting portion 64. Thereafter, air and the like in the flow channel is excluded by purging again with the use of oxygen gas.

A quantitative analysis for elements is then carried out. The laser beam 71 is irradiated to a predetermined site of the above described bottom surface 63a (a portion to be analyzed) while supplying oxygen gas into the cell space 62, and more specifically, while jetting oxygen gas to the bottom surface 63a of the steel sample 63 from the extreme end of the gas jetting nozzle 74. In this case, it is preferred that the laser beam 71 is irradiated so as to focus on a position which deviates from the bottom surface 63a of the steel sample 63 by several $\mu$m towards the inside of the cell space 62, and that the bottom surface 63a is scanned along X-Y direction as a result of operating the three-dimensional stage 68.

The portion to be analyzed of the steel sample 63 which has been irradiated by the laser beam 71 in the above described oxygen stream reaches a high temperature, so that C and S contained in the steel sample 63 are burned up by means of oxygen to produce CO gas, $CO_2$ gas, and $SO_3$ gas, respectively. A gas G containing these gases flows into a produced gas flow passage 81 through a gas outlet 80 with the aid of oxygen gas as a carrier gas. In this case, both the three-way electromagnetic valves 83 and 85 in the produced gas flow passage 81 are turned on, so that a bypass flow passage 87 is in a closed state.

Accordingly, the CO gas, the $CO_2$ gas, and the $SO_2$ gas flow through the dust filter 82, the three-way electromagnetic valve 83, the dehumidifier 84, and the three-way electromagnetic valve 85, and finally the gases reach the sampling section 86. In this occasion, oxidized dust such as iron oxide contained in the CO gas, the $CO_2$ gas, and the $SO_2$ gas is removed by the dust filter 82, and water vapor is removed in the dehumidifier 84. Accordingly, the gas G in the former part of the sampling section 86 contains CO, $CO_2$, and $SO_2$ as its components.

The gas G containing the above described CO, $CO_2$, and $SO_2$ is sampled at a constant interval and constant amount in the sampling section 86, and these samples are fed to an ionizing section 13 of the mass spectrometer 12. In the ionizing section 13, CO, $CO_2$, and $SO_2$ are ionized to $CO^+$ (m/z=28), $CO_2^+$ (m/z=44), and $SO_2^+$ (m/z=64), respectively, and they are subjected to mass spectrometric analysis in an analyzing section 24. Based on the results obtained, an amount of C and S can be obtained.

After conducting a mass spectrometric analysis through effecting a laser irradiation for a required period of time, a weight of the steel sample 63 is measured, and a difference between the present weight and the weight of the steel sample 63 obtained immediately after the above described preliminary irradiation is used as a weight of the sample. As a result, a content of C and S in the sample can be determined on the basis of the weight which was finally obtained and the above described amounts of C and S measured.

In order to measure each amount of N and H (content) contained in the steel sample 63, an inert gas (for example, argon gas) is used in place of oxygen gas. Also in the case of measuring N and H, the flow channel extending from the irradiation cell 61 to the mass spectrometer 12 is purged by means of argon gas, and a similar preliminary irradiation is made upon the steel sample 63 to clean the steel sample 63 prior to analysis of these N and H as in the above described case of C and S.

After measuring a weight of the above described steel sample 63, it is set on the sample resting portion 64. Thereafter, air and the like in the flow channel is excluded by purging again with the use of argon gas. The laser beam 71 is irradiated to a predetermined site of the bottom surface 63a (a portion to be analyzed) of the steel sample 63 while supplying argon gas into the cell space 62. The portion to be analyzed of the steel sample 63 which has been irradiated by the laser beam 71 in the argon gas stream as described above comes to be a high temperature, so that N and H contained in the steel sample 63 are changed to $N_2$ gas, and $H_2$ gas, respectively. A gas G containing these gases $N_2$ and $H_2$ flows into a gas flow passage 81 through a gas outlet 80 with aid of argon gas as a carrier gas. In this case, both the three-way electromagnetic valves 83 and 85 in the gas flow passage 81 are turned off, so that a bypass flow passage 87 is in an opened state. Accordingly, the above described gas G containing $N_2$ gas, and $H_2$ gas flows through the dust filter 82, the three-way electromagnetic valve 83, a bypass flow channel 87, and the three-way electromagnetic valve 85, and finally the gas G reaches the sampling section 86. In this occasion, dust contained in the $H_2$ gas and the like is removed by the dust filter 82. Accordingly, the gas G in the former part of the sampling section 86 contains $N_2$, and $H_2$ as its components.

When the gas G is sampled at a constant interval in a constant amount in the sampling section 86 and these samples are fed to the mass spectrometer 12, amounts of N and H can be measured. In this case also, when weights of the steel sample 63 before and after irradiating laser beam while jetting argon gas to a portion to be analyzed of the steel sample 63 are measured, contents of N and H in the steel sample 63 can be also determined.

As mentioned above, since the element analyzer is constituted so that the laser beam 71 is irradiated onto the metal sample 63 in an oxygen or inert gas stream to produce gases, and these gases are introduced to the mass spectrometer 12 together with the oxygen gas or the inert gas, unlike a conventional element analyzer wherein a weighed metal sample is placed in a graphite crucible, a problem of an erroneous or blank value due to contamination in case of employing a graphite crucible and the like is solved, so that even in the case where C, S, N, and H are merely contained in the metal sample 63 at a slight amount (ppm or less), respectively, these components can be quantitatively analyzed precisely and positively.

As is understood from the above description, the flow channel extending from the irradiation cell 61 to the mass spectrometer 12 is purged, and the metal sample 63 is cleaned over a wide range including a portion to be analyzed therein before conducting a quantitative analysis, so that a result of measurement with high precision can be obtained in the present preferred embodiment, although it is not required for consideration with respect to contamination in case of arranging or the handling of a sample.

Furthermore, in the aforementioned embodiment, a detecting section for detecting gas components is sufficient for only one mass spectrometer 12, it is not required to provide a plurality of analyzing sections each having a different measuring principle unlike the arrangements in the prior art. Moreover, there is a remarkable advantage in that C and S/N and H can be analyzed by one analyzing section by means of switching a gas to be supplied to the irradiation cell 61 to the other.

In the above-mentioned preferred embodiment, although it has been constituted so that either oxygen gas or an inert gas may be selectively supplied with respect to the internal space 62 of the irradiation cell 61, merely either of an oxygen gas cylinder or an inert gas cylinder 90 may be joined to the upstream of the gas feed passage 75 through valve 89 as shown in FIG. 16 instead of the above described arrangement. For instance, when the oxygen gas cylinder 90 is coupled upstream of the gas feed passage 75, oxygen gas is fed to the internal space 62 of the irradiation cell 61, so that at least either one of C and S contained in the metal sample 63 can be analyzed quantitatively. On the other hand, when the inert gas cylinder 90 is coupled the upstream of the gas feed passage 75, at least either one of N and H contained in the metal sample 63 can be analyzed quantitatively.

While the mass spectrometer 12 has been employed as a detecting section in the aforementioned embodiment, another detecting mechanism may be utilized in place of the mass spectrometer 12. More specifically, in case of feeding oxygen gas to the irradiation cell 61, NDIR may be used, while when an inert gas is passed through the irradiation cell 61, a thermal conductivity meter may be utilized.

Figure 17:
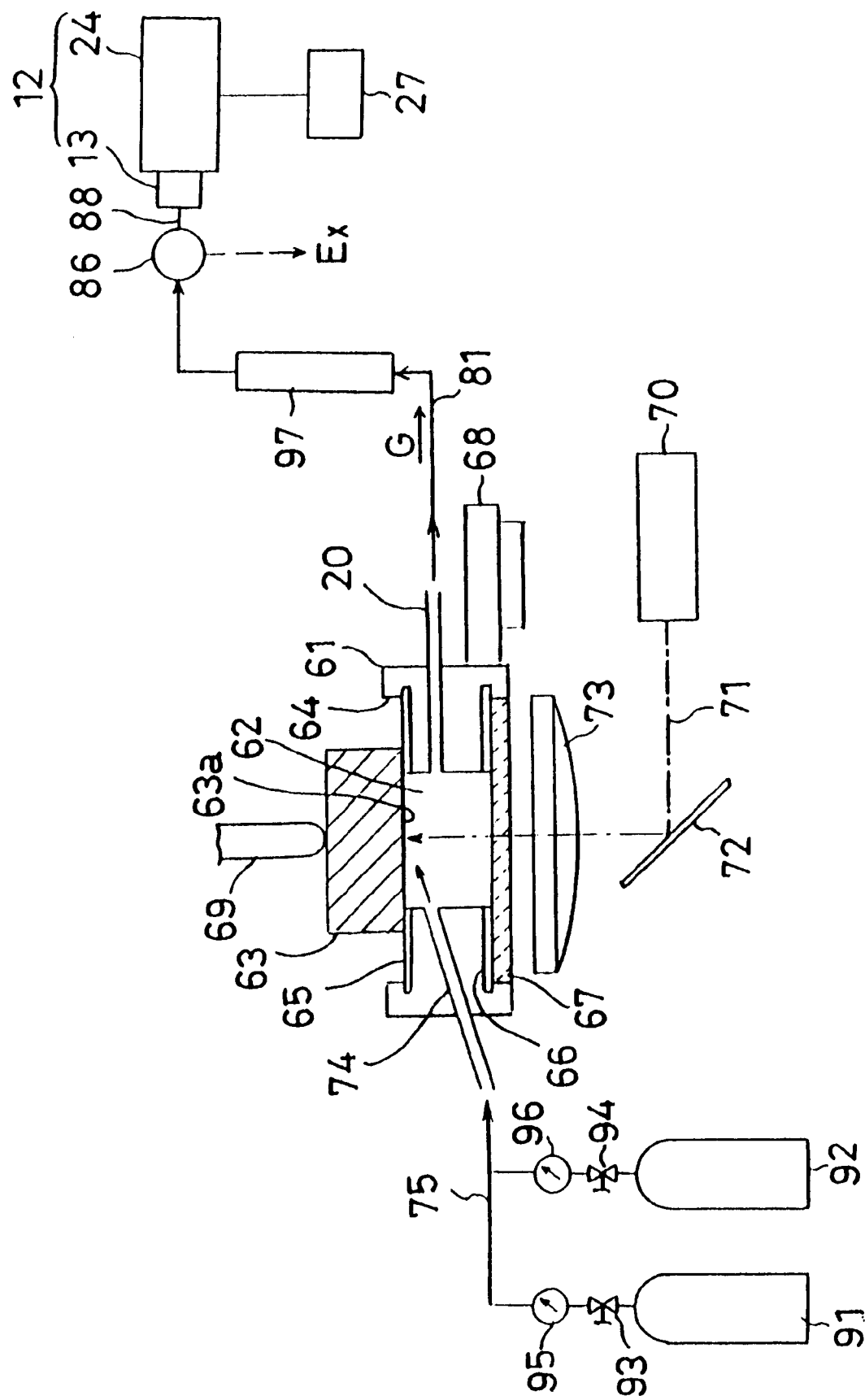
FIG. 17 is a view showing schematically a constitution of the system for analyzing elements in a preferred embodiment according to the seventh embodiment.

FIG. 17 shows a preferred embodiment according to a seventh embodiment wherein an element analyzer of the present embodiment can analyze at least any one element of C, S, and N. In the system for analyzing elements shown in FIG. 17, a gas prepared by admixing hydrogen gas with a basic inert gas at a certain ratio (for example, hydrogen gas: inert gas=2:8) is supplied to an irradiation cell 61. In FIG. 17, reference numerals 91, and 92 designate a hydrogen gas cylinder, and an inert gas cylinder, respectively, and they are connected to a gas flow passage 75 through flow regulating valves 93 and 94 as well as flow meters 95 and 96, respectively. Furthermore, reference numeral 97 denotes a dehydrator having a function for removing a dust filter and disposed on a produced gas flow passage 81. It is to be noted that the constitutional components other than those described above are the same with that shown in FIG. 15, so that they are designated by the same reference numerals as that of FIG. 15.

In the following, operation of the element analyzer having the above described constitution will be described and steel is used as a metal sample 63. A steel material to be analyzed is cut out by means of a cutter into a block-shaped piece having a suitable dimension, the cut out surface thereof is ground sufficiently by the use of a sandpaper to prepare the metal sample 63. The metal sample 63 thus prepared is set on a sample resting portion 64 of the irradiation cell 61 so that a plane 63a thus ground of the metal sample 63 is directed in a downward direction.

In this embodiment, purging of air and the like, and preliminary irradiation of laser beam are carried out before conducting quantitative analysis of elements. More specifically, the valves 93 and 94 are opened to supply a gas prepared by admixing oxygen gas with an inert gas (for example, argon gas) in a ratio of about 2:8 (hereinafter referred to simply as "mixed gas") to the cell space 62 of the irradiation cell 61, whereby a flow channel extending from the irradiation cell 61 to the mass spectrometer 12 is purged, so that air and the like remaining in the flow channel is exhausted. Thereafter, the laser oscillator 70 is operated to irradiate the laser beam 71 onto the bottom surface 63a of the steel sample 63 under a state where the mixed gas is supplied to the cell space 62, whereby contamination produced at the time of cutting, grinding, or handling of the bottom surface 63a is removed. In the preliminary radiation for cleaning a sample, it is preferred to irradiate the bottom surface 63a of the steel sample 63 over a wider range than that in case of analysis thereof by such a manner that the three-dimensional stage 68 is operated to transfer suitably the irradiation cell 61 together with the steel sample 63 in two-dimensional directions, or to change an angle of the mirror 72.

When the above described preliminary irradiation is completed, the steel sample 63 which has been cleaned is removed from the sample resting portion 64, the steel sample 63 thus removed is weighed, and then it is set on the sample resting portion 64. Thereafter, air and the like in the flow channel is excluded by purging again the same with the use of the mixed gas.

A quantitative analysis for elements is carried out in accordance with the manner as described hereinafter. The laser beam 71 is irradiated to a predetermined site of the above described bottom surface 63a (a portion to be analyzed) while supplying the mixed gas into the cell space 62, and more specifically, while jetting the mixed gas to the bottom surface 63a of the steel sample 63 from the extreme end of the gas jetting nozzle 74. In this case, it is preferred that the laser beam 71 is irradiated so as to focus on a position which deviates from the bottom surface 63a of the steel sample 63 by several $\mu$m towards the inside of the cell space 62, and that the bottom surface 63a is scanned along X-Y directions as a result of operating the three-dimensional stage 68.

The portion to be analyzed of the steel sample 63 which has been irradiated by the laser beam 71 in the above described mixed gas stream reaches a high enough temperature to be vaporized, so that C, S, and N contained in the steel sample 63 can react with the hydrogen gas contained in the mixed gas to produce $CH_4$, $H_2S$, and $NH_3$, respectively. A gas G containing these gases flows into a gas flow passage 81 through a gas outlet 80 with aid of the mixed gas as a carrier gas. At a point halfway thereof, dust and/or moisture are removed by a dehydrator 97 having a function to act also as a dust filter. Accordingly, the gas G in the former part of the sampling section 86 contains $CH_4$, $H_2S$, and $NH_3$ as its only components.

The gas G containing the above described $CH_4$, $H_2S$, and $NH_3$ is sampled at a constant interval in constant amounts in the sampling section 86, and these samples are fed to an ionizing section 13 of the mass spectrometer 12. In the ionizing section 13, $CH_4$, $H_2S$, and $NH_3$ are ionized to $CH_4^+$ (m/z=16), $H_2S+$(m/z=34), and $NH_3^+$ (m/z=17), respectively, and they are subjected to a mass spectrometric analysis in an analyzing section 24. Based on the results obtained, the amounts of C, S, and N can be obtained.

After conducting mass spectrometric analysis through effecting laser irradiation for a required period of time, the weight of the steel sample 63 is measure and a difference between the present weight and the weight of the steel sample 63 obtained after the above described preliminary irradiation is used as a weight of the sample. As a result, a content of C, S, and N in the sample can be determined on the basis of the weight which was finally obtained and the above described amounts of C, S, and N measured.

According to the element analyzer of the present preferred embodiments, the following advantages are obtained. Namely, since the element analyzer according to the present embodiment is constituted so that the laser beam 71 is irradiated onto the metal sample 63 in a mixed gas (a basic inert gas containing hydrogen gas) stream to produce $CH_4$, $H_2S$, $NH_3$ and the like gases, and these gases are introduced to the mass spectrometer 85 together with the above described mixed gas unlike a conventional system for analyzing elements wherein a weighed metal sample is placed in a graphite crucible. Accordingly, a problem of blank value readings due to contamination in the case of employing a graphite crucible and the like is solved, so that even in a case where C, S, and N are merely contained in the metal sample 63 at a slight amount (ppm or less), respectively, these components can be quantitatively analyzed precisely and positively.

As is understood from the above description, a flow channel extending from the irradiation cell 61 to the mass spectrometer 12 is purged, and the metal sample 63 is cleaned over a wide range including a portion to be analyzed therein before conducting a quantitative analysis, so that a measurement with high precision can be obtained in the present preferred embodiments, although contamination in the case of handling a sample is not considered.

Furthermore, in the aforementioned preferred embodiments according to the fourth to the seventh embodiments, only one mass spectrometer 12 is sufficient therefor as a detecting section for detecting gas components, so that it is not required to provide a plurality of analyzing sections each having a different measuring principle unlike arrangements in the prior art.

Moreover, in the above described preferred embodiments according to the fourth to the seventh embodiments, a mass spectrometer of time of flight (TOF-MS) type may be employed in place of the above described mass spectrometer 12 of a so-called Q-MS type. In this case, since it is required to sample instantaneously the gas G, it is preferred to arrange a pulse-formed electric field for the gas in case of, for example, ionizing the same in the electric field, so that only the gas which is ionized is introduced into the TOF-MS.

Besides, in the preferred embodiments, it may be arranged so that the gas G produced in the irradiation cell 61 is introduced to the mass spectrometer 12 without any processing (the gas is not passed through the filters 82 and 97), and in such a case, Fe (iron) can be detected in the mass spectrometer 12.

Figure 18:
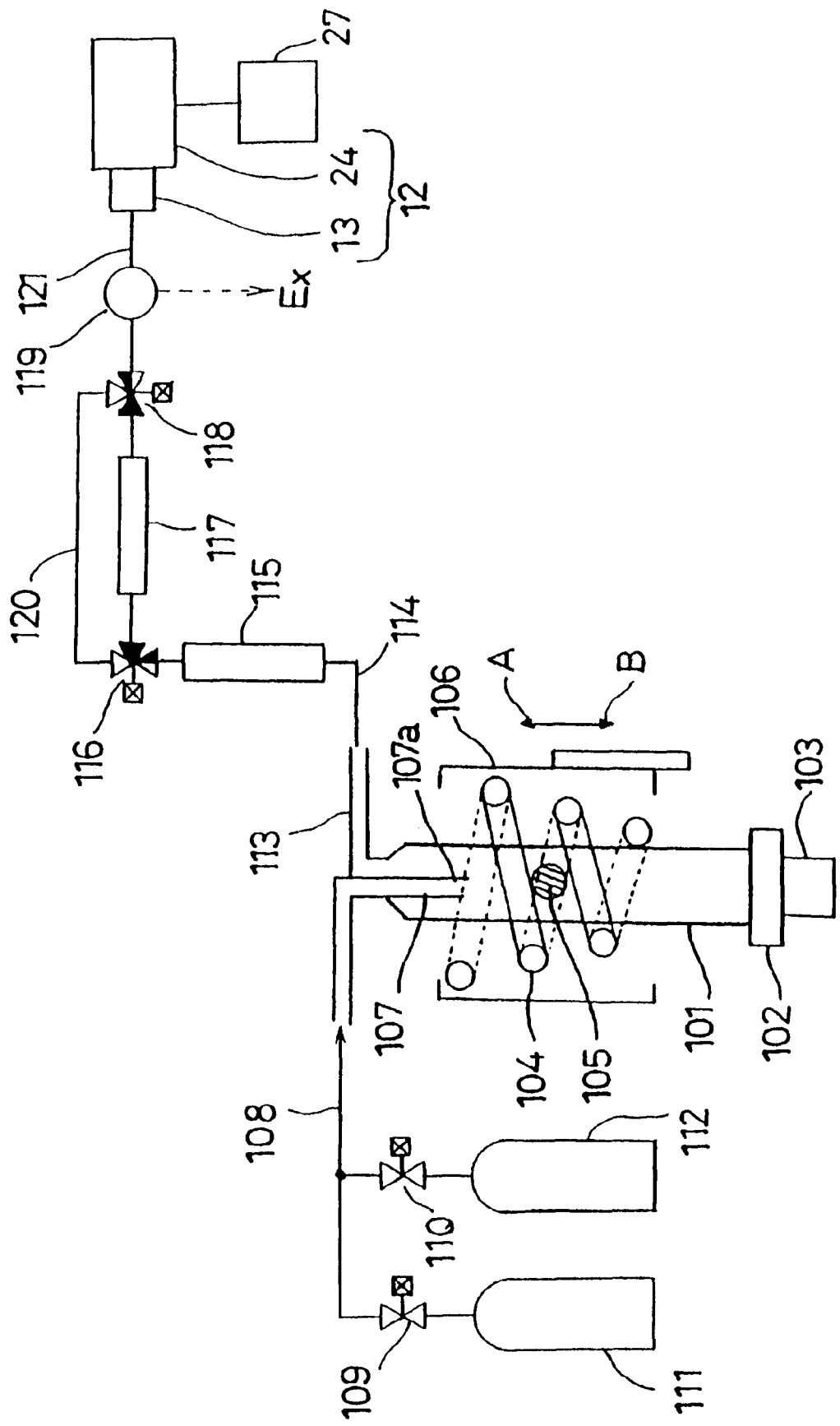
FIG. 18 is a view showing schematically a constitution of the system for analyzing elements in a preferred embodiment according to the eighth embodiment.

FIG. 18 shows a preferred embodiment according to an eighth embodiment of the invention wherein the element analyzer in the present embodiment can analyze quantitatively at least any one element of C, S, N, and H.

In FIG. 18, reference numeral 101 designates a cylindrical extracting cell having, for example, 20 mm inner diameter and 130 mm length, and made of a quartz tube which is disposed vertically. Reference numeral 102 denotes a sample holder functioning also as a member for sealing a lower opening of the extracting cell 101, and which is transferred in a vertical direction (indicated by arrows A and B) by means of a vertically moving mechanism 103, thereby to seal or release the lower opening of the extracting cell 101. Reference numeral 104 designates a high-frequency coil (referred to also as "levitation coil") for levitating a metal sample 105 and heating to melt the same as it stands, The coil is transferred in a vertical direction along the longitudinal direction of the extracting cell 101 (in the direction along arrows A and B) by means of a vertically moving mechanism 106, and is stopped at a desired position. To the high-frequency coil 104 is connected a high-frequency power source which is not shown.

Reference numeral 107 denotes a gas jetting nozzle for introducing a gas into the extracting cell 101, the end 107a of which is directed to a downward direction, and to the upstream side of which is joined a gas feed passage 108. Further, an inert gas cylinder 111 and an oxygen gas cylinder 112 are coupled to the gas feed passage 108 through valves 109 and 110, respectively.

Reference numeral 113 designates a gas exhaust pipe for taking out a gas produced in the extracting cell 101, and to the downstream side of which is connected a gas flow passage 114. Moreover, the gas flow passage 114 is provided with a dust filter 115 for removing oxidized dust such as iron oxide contained in the produced gas, a three-way electromagnetic valve 116, a dehumidifier 117 for removing water vapor (moisture) contained in the produced gas, a three-way electromagnetic valve 118, and a sampling section 119, respectively. Further, reference numeral 120 denotes a gas flow passage disposed to communicate the three-way electromagnetic valve 116 with the three-way electromagnetic valve 118 so as to bypass the dehumidifier 117. Either of portions on the downstream side of the-sampling section 119 is connected to the above described mass spectrometer 12 through a flow channel 121, while the other portion is connected to an exhaust section (not shown).

In the following, operation of the element analyzer having the above described constitution will be described wherein steel is employed as the metal sample 105. The steel being an object to be analyzed is cut out by means of a cuter to obtain a columnar or spherical piece having a suitable dimension (a weight of which is about 1.5 g). The metal sample 105 thus obtained is rested on a sample holder 102.

Then, the sample holder 102 is raised along a direction indicated by the arrow A to position the metal sample 105 in the extracting cell 101, and the lower opening of the extracting cell 101 is closed at the same time. The valve 109 is opened to feed an inert gas (for example, helium gas) from the gas jetting nozzle 107 into the extracting cell 101 while maintaining this situation.

The high-frequency coil 104 is lowered in a direction indicated by the arrow B to position the metal sample 105 inside the high-frequency coil 104 while keeping the above described situation. In this situation, when a high-frequency current is applied to the high-frequency coil 104, an upward force (in a direction indicated by the arrow A) acts upon the metal sample 105 by means of an interaction between an induction current induced by the metal sample 105 and a magnetic field of the high-frequency coil 104, whereby the metal sample 105 is levitated (high-frequency levitation) in the extracting cell 101 while maintaining a balance with the gravitational force. Thus, it is adjusted so that the high-frequency coil 104 is transferred upwardly to position the metal sample 105 levitated by high-frequency at a position where it is 10 to 20 mm downward from a nozzle hole 107a of the gas jetting nozzle 107 which is jetting helium gas.

On the other hand, an induction current flows through the metal sample 105 itself at the same time of the above described levitation to produce Joule heat, whereby the metal sample 105 is heated to a molten state. It is preferred to control heating of the metal sample 105 at a temperature of up to 1000° C. by adjusting a magnitude of a high-frequency current applied to the high-frequency coil 104. As mentioned above, when the metal sample 105 is molten in a helium gas stream, H contained in the metal sample 105 is extracted in the form of $H_2$ gas.

The $H_2$ gas produced as mentioned above flows into a produced gas flow passage 114 through a gas taking-out pipe 113 with the aid of helium gas as a carrier gas. In this case, both the three-way electromagnetic valves 116 and 118 in the produced gas flow passage 114 are turned off, so that a bypass flow passage 120 is in an opened state. Accordingly, the above described $H_2$ gas and the like flow through the dust filter 115, the three-way electromagnetic valve 116, a bypass flow channel 120, and the three-way electromagnetic valve 118, and finally these gases reach the sampling section 119. In this occasion, dust contained in the above described $H_2$ gas and the like is removed by the dust filter 115. Accordingly, the gas in the former part of the sampling section 121 contains $H_2$ as its components.

The gas containing $H_2$ is sampled at a constant interval in constant amounts in the sampling section 119, and these samples are fed to an ionizing section 13 of the mass spectrometer 12. In the ionizing section 13, $H_2$ is ionized to $H_2^{30}$ (m/z=2), and it is subjected to mass spectrometric analysis in an analyzing section 24. Based on the results obtained, an amount of H can be obtained.

When the extraction of $H_2$ at a temperature of 1000° C. or less is finished, a gas to be fed to the extracting cell 101 is switched from helium gas to oxygen gas. In other words, the valve 109 is closed, while the valve 110 is opened.

Under the condition where oxygen gas is supplied to the above described extracting cell 101 through the gas jetting nozzle 107, a magnitude of high-frequency current to be applied to the high-frequency coil 104 is increased to burn up the metal sample 105 at a temperature of 1000° C. or more. As mentioned above, when the metal sample 105 is burned up in oxygen gas stream, $CO_x(CO, CO_2)$, $SO_x(SO_2, SO_3)$, and $NO_x(N_2O, NO, NO_2, \ldots)$ are produced.

The gases $CO_x$, $SO_x$, and $NO_x$ produced as mentioned above flow into the produced gas flow passage 114 through the gas taking-out pipe 113 with the aid of oxygen gas as a carrier gas. In this case, both the three-way electromagnetic valves 116 and 118 in the produced gas flow passage 114 are turned on, so that the bypass flow passage 120 is in a closed state. Accordingly, the above described gases $CO_x$, $SO_x$, $NO_x$ and the like flow through the dust filter 115, the three-way electromagnetic valve 116, a dehumidifier 117, and the three-way electromagnetic valve 118, and finally these gases reach the sampling section 119. In this occasion, oxidized dust such as iron oxide contained in the above described $CO_x$, $SO_x$, $NO_x$ and the like gases is removed by the dust filter 115, while water vapor is removed by the dehumidifier 117. Accordingly, the gas in the former part of the sampling section 121 contains $CO_x$,$SO_x$ and $NO_x$ as its components.

The above described gas containing $CO_x$, $SO_x$ and $NO_x$ is sampled at a constant interval in constant amounts in the sampling section 119, and these samples are fed to the ionizing section 13 of the mass spectrometer 12. In the analyzing section 24, they are subjected to mass spectrometric analysis. Based on the results obtained, each amount of C, S, and N can be obtained.

As mentioned above, the element analyzer according to the present preferred embodiments is constituted so that the metal sample 105 is subjected to levitating fusion in an inert gas or an oxygen gas stream, and the gas containing $H_2$ or $CO_x$, $SO_x$ and $NO_x$ produced at that time is introduced to the mass spectrometer 12 together with the above described inert gas or oxygen gas unlike a conventional element analyzer wherein a weighed metal sample is placed in a graphite crucible, so that a problem of blank value due to contamination in case of employing a graphite crucible and the like is solved, and hence, even in the case where C, S, N, and H are merely contained in the metal sample 105 at a slight amount (ppm or less), respectively, these components can be analyzed quantitatively in a precise and positive manner.

Furthermore, in the aforementioned preferred embodiment, since one mass spectrometer 12 is sufficient as a detecting section for detecting gas components, it is not required to provide a plurality of analyzing sections each having a different measuring principle unlike an arrangement in the prior art. Moreover, there is a remarkable advantage in that elements C, S, N, and H can be analyzed in a single analyzing section by merely switching a gas to be supplied to the extracting cell 101 with another gas.

Since the above described embodiment is arranged so that the high-frequency coil 104 transfers vertically along the longitudinal direction of the extracting cell 101, it is not required to separately provide a means for positioning the metal sample 105 at a predetermined site of the high-frequency coil 104. Thus, the potential of contamination from a crucible is eliminated and an induction current will flow directly through the metal sample for heating and melting the metal sample.

In the aforementioned embodiment, although an inert gas or oxygen gas has been supplied to the extracting cell 101 by switching from one source to another source, either one of an inert gas and oxygen gas may be supplied to the extracting cell 101 instead of the former arrangement.

Figure 19:
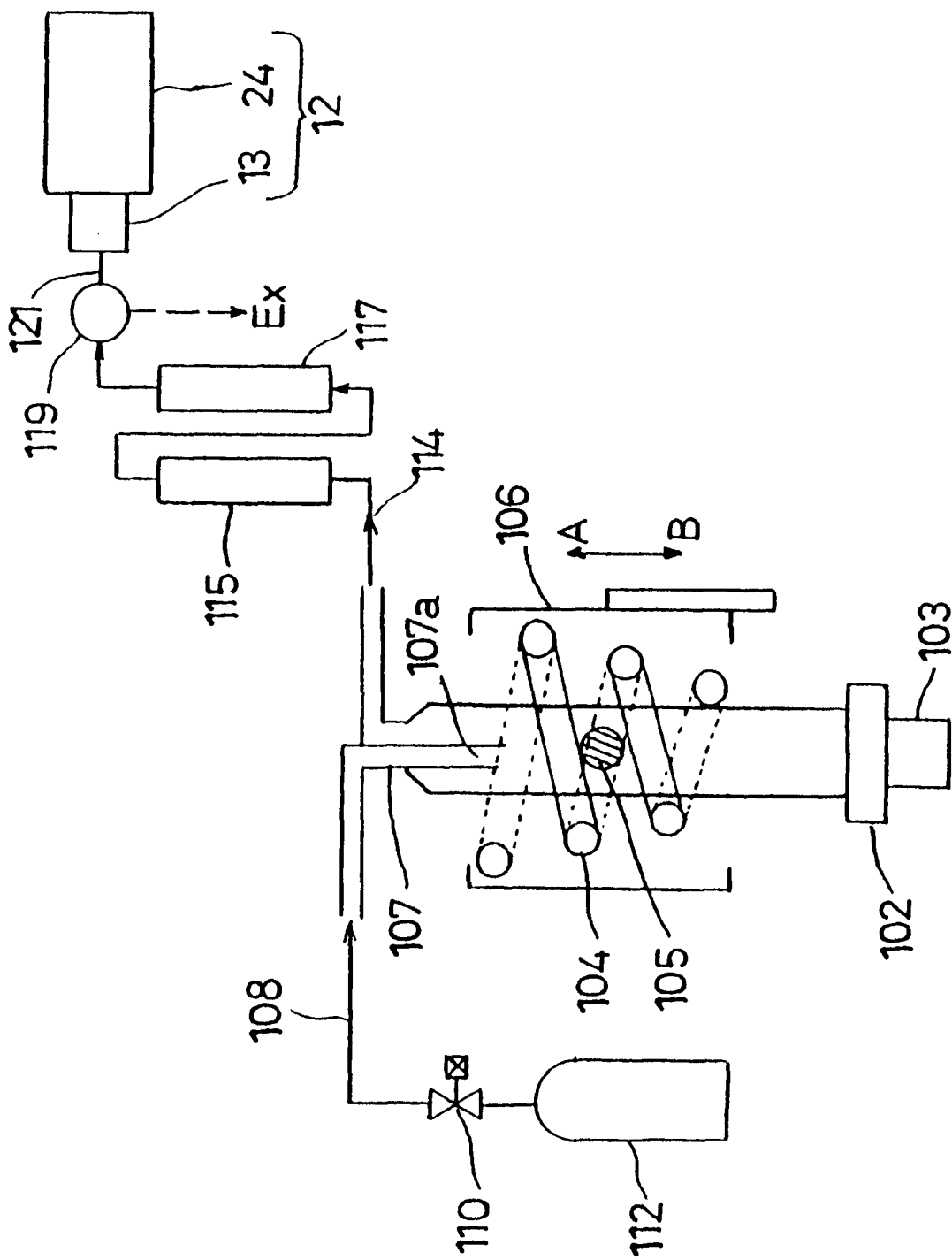
FIG. 19 is a view showing schematically a constitution of the system for analyzing elements in a preferred embodiment according to the ninth embodiment.

FIG. 19 shows a preferred embodiment according to a ninth embodiment of the invention, and more specifically, oxygen gas is supplied to an extracting cell 101, that is, an oxygen gas cylinder 112 is coupled to a gas feed passage 108 joined to the extracting cell 101. When the system is constituted as described above, quantitative analysis of C, S, and N contained in the metal sample 105 can be conducted as is understood from the above description, so that the constitution in the produced gas feed passage 114 becomes simple.

Furthermore, in the element analyzer shown in FIG. 19, when an inert gas cylinder is connected to the gas feed passage 108 in place of the oxygen gas cylinder 112 and further, the dehumidifier 117 removed, H in the metal sample 105 can be quantitatively analyzed.

The present invention is not limited to the above described embodiments, for example, the high-frequency coil 104 can be fixedly disposed instead of transferred in a vertical direction, and the sample holder 102 is transferred vertically in the extracting cell 101 so that the metal sample 105 may be positioned at a predetermined site of the high-frequency coil 104.

In preferred embodiments, a mass spectrometer of a time of flight (TOF-MS) type may be employed in place of the above described mass spectrometer 12 of a so-called Q-MS type. In this case, since it is required to sample instantaneously the produced gas G, it is preferred to arrange a pulse-formed electric field to be prepared for the gas in case of, for example, ionizing the gas in the electric field, and only the gas ionized is introduced into the TOF-MS.

According to the present invention, elements such as C, S, O, N, H and the like, even in a slight amount, respectively, in a raw material such as steel, ceramics and the like, can be quantitatively analyzed positively at high sensitivity and order of weight ppm or less, for example, 0.1 to 0.01 ppm.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A system for analyzing elements in a sample comprising:
   a combustion member comprising one of a high-frequency heating furnace and an electric resistance furnace for receiving the sample;
   a source of oxygen gas connected to the combustion member to supply oxygen gas to the combustion member as the sample is heated to gasify the elements in the sample;
   a sample section connected to the heating member by an exhaust conduit for sampling at a constant interval and at constant amounts;
   a dust filter unit operatively connected to the exhaust conduit for removing dust;
   an oxidizing device operatively connected to the exhaust conduit for oxidizing the gas output of the combustion member;
   a dehumidifier for dehumidifying the gas output before the gasified elements are analyzed;
   a mass spectrometer;
   a conduit connecting the sampling section to the mass spectrometer whereby the gasified elements are analyzed quantitatively by the mass spectrometer to determine at least an element of C, S, and N to an accuracy of 0.1 ppm, and
   a feedback circulating system for recirculating the gasified elements from the exhaust conduit to the combustion member until all of the elements in the sample are gasified.

2. A system for analyzing elements in a sample comprising:
   an electric resistance furnace for receiving a sample;
   a source of hydrogen gas connected to the electric resistance furnace to supply hydrogen gas as the sample is heated to gasify the elements in the samples;
   a sampling section for sampling the gasified elements at a constant interval and at constant amounts;
   a feedback circulating system for recirculating the gasified elements to the electric resistance furnace until all of the elements in the sample are gasified;
   means for providing an electric field to ionize the gasified elements prior to an introduction into the mass spectrometer; and
   a mass spectrometer connected to the sampling section for receiving the gasified elements whereby a quantitative analysis of the amount of elements are determined.

3. A system for analyzing elements in a steel specimen comprising:
   a combustion member for receiving the steel sample;
   a source of oxygen gas connected to the combustion member to supply oxygen gas to the combustion member as the sample is heated to gasify the elements in the sample;
   an exhaust channel from the combustion member for removing the gasified elements;
   a dust filter unit operatively connected to the exhaust channel, for removing any oxidized dust;
   a dehumidifier, operatively connected to the exhaust channel, for removing water vapor;
   an oxidizing device, operatively connected to the exhaust channel, for oxidizing any CO contained in the gasified elements;
   a sampling section connected to the exhaust channel for sampling at a constant interval and at constant amounts of gasified elements;
   a mass spectrometer connected to the sampling section whereby the gasified elements are analyzed quantitatively to determine the elements in the steel specimen; and
   a feedback circulating passage connected to the heating member and downstream of the dust filter unit, dehumidifier unit and the oxidizing device and upstream of the mass spectrometer to provide a return of the gasified elements to provide reheating in the heating member.

4. The system of claim 3 further including a suction pump operatively connected in the feedback circulating passage to feedback the gasified elements until the steel sample is completely combusted.

5. The system of claim 4 further including a valve member for selectively connecting the exhaust channel to either the feedback circulating passage to the mass spectrometer.

6. The system of claim 5 wherein the heating member is selected from one of a high-frequency heating furnace and an electric resistance furnace.

7. The system of claim 4, wherein the mass spectrometer analyzes the gasified elements to an accuracy of 0.1 ppm.

8. A system for analyzing elements of C, S and N in a sample comprising:
   a combustion member comprising one of a high-frequency heating furnace and an electric resistance furnace for receiving the sample;
   a source of oxygen gas connected to the combustion member to supply oxygen gas to the combustion member as the sample is heated to gasify the elements in the sample;

a sample section connected to the heating member by an exhaust conduit for sampling at a constant interval and at constant amounts;

a feedback circulating system connected to the sampling section for recirculating the gasified elements from the exhaust conduit to the combustion member until all of the elements in the sample are gasified;

a dust filter unit operatively connected to the exhaust conduit for removing dust;

an oxidizing device operatively connected to the exhaust conduit for oxidizing the gas output of the combustion member;

a dehumidifier for dehumidifying the gas output before the gasified elements are analyzed;

a mass spectrometer; and a conduit connecting the sampling section to the mass spectrometer whereby the gasified elements are analyzed quantitatively by the mass spectrometer to determine at least an element of C, S, and N to an accuracy of 0.1 ppm.

9. The system of claim 8 further including means for providing an electric field to ionize the gasified elements prior to an introduction into the mass spectrometer including a heatable filament, an electron collecting electrode, an ion producing electrode, and an ion extracting electrode.

10. A system for analyzing elements of C, S and N in a metal sample comprising:

a crucible;

a source of a metal sample;

a combustion member comprising one of a high-frequency heating furnace and an electric resistance furnace for receiving the metal sample in the crucible;

a source of oxygen gas connected to the combustion member to supply oxygen gas to the combustion member as the sample is heated to gasify the elements in the sample;

a sample section, having an exhaust port, connected to the heating member by an exhaust conduit for sampling the gasified elements at a constant interval and at constant amounts;

a feedback circulating system connected to the sampling section for recirculating the gasified elements from the exhaust conduit to the combustion member until all of the elements in the sample are gasified;

a dust filter unit operatively connected to the exhaust conduit for removing dust;

an oxidizing device operatively connected to the exhaust conduit for oxidizing the gas output of the combustion member;

a dehumidifier for dehumidifying the gas output before the gasified elements are analyzed;

a mass spectrometer; and a conduit connecting the sampling section to the mass spectrometer, the sampling section alternatively releasing the gasified elements through first the exhaust port at first constant intervals and constant amounts and directing the gasified elements to the conduit at second constant intervals and second constant amounts whereby the gasified elements are analyzed quantitatively by the mass spectrometer to determine at least an element of C, S, and N to an accuracy of 0.1 ppm.

* * * * *